United States Patent [19]

Imran

[11] Patent Number: 5,479,934
[45] Date of Patent: Jan. 2, 1996

[54] EEG HEADPIECE WITH DISPOSABLE ELECTRODES AND APPARATUS AND SYSTEM AND METHOD FOR USE THEREWITH

[75] Inventor: Mir A. Imran, Palo Alto, Calif.

[73] Assignee: Physiometrix, Inc., No. Billerica, Md.

[21] Appl. No.: 126,113

[22] Filed: Sep. 23, 1993

Related U.S. Application Data

[63] Continuation of Ser. No. 790,412, Nov. 8, 1991, abandoned.

[51] Int. Cl.⁶ .................................................. A61B 5/0478
[52] U.S. Cl. ........................... 128/731; 607/139; 128/644
[58] Field of Search ..................................... 128/731, 732, 128/644; 607/139, 140

[56] References Cited

U.S. PATENT DOCUMENTS

| | | | |
|---|---|---|---|
| 3,623,477 | 11/1971 | Trent | 128/731 |
| 3,998,213 | 12/1976 | Price | 128/380 |
| 4,279,258 | 7/1981 | John | 128/731 |
| 4,753,242 | 6/1988 | Saggers | 128/380 |
| 4,967,038 | 10/1990 | Gevins et al. | 128/731 |
| 5,265,607 | 11/1993 | Moberg | 128/731 |
| 5,291,888 | 3/1994 | Tucker | 128/644 |

*Primary Examiner*—William E. Kamm
*Assistant Examiner*—Scott M. Getzow
*Attorney, Agent, or Firm*—Flehr, Hohbach, Test, Albritton & Herbert

[57] ABSTRACT

Headpiece for making EEG measurements on the head of a patient in the form of a human being utilizing electrode positioning system requiring the use of a plurality of electrodes in predetermined anatomical positions on the head comprising a plurality of longitudinally extending and transversely extending strips of an elastic material to form a pattern having openings therein. A plurality of electrode assemblies are mounted on the strips in spaced-apart positions. Straps are secured to the strips for securing said strips and the electrode assemblies mounted thereon to the head of the patient by stretching of the strips so that the electrode assemblies are positioned in the desired anatomical positions on the head regardless of the size of the head of the human being.

27 Claims, 12 Drawing Sheets

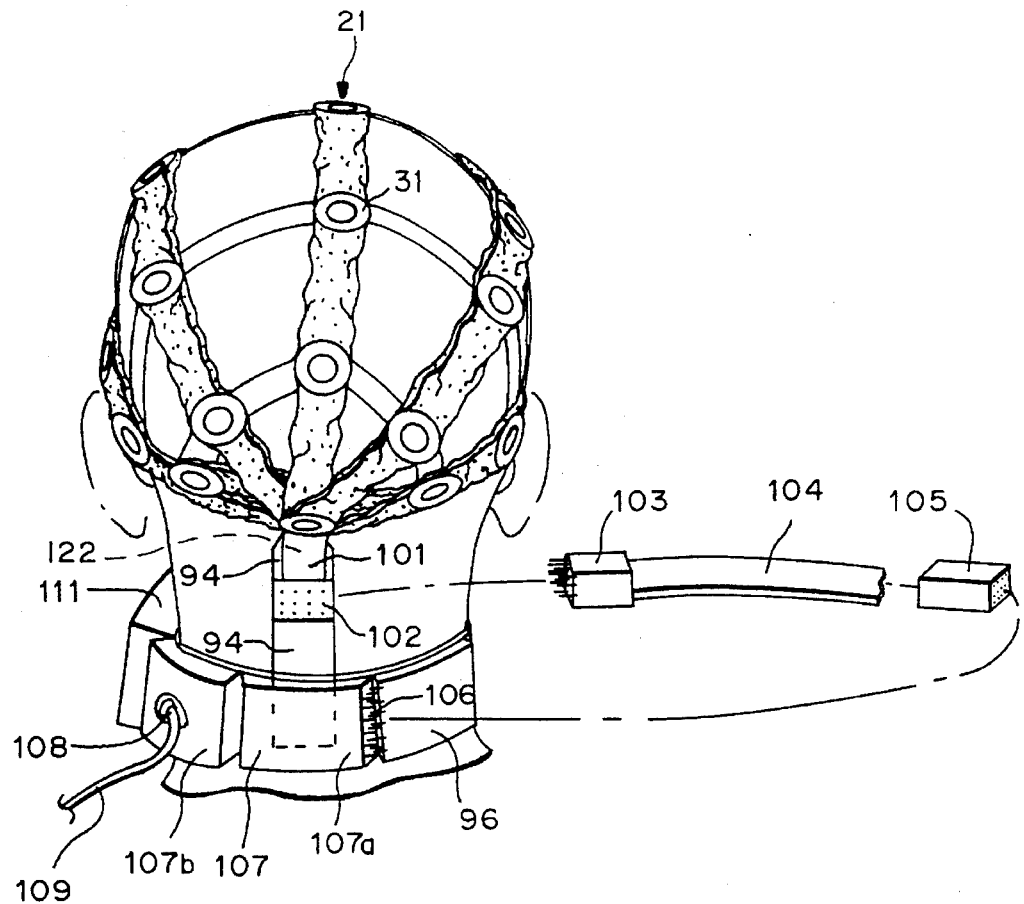
FIG.—5
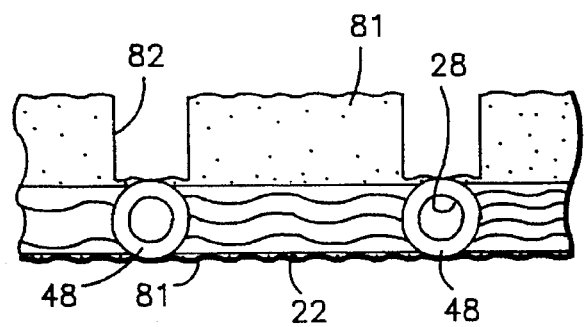
FIG.—7
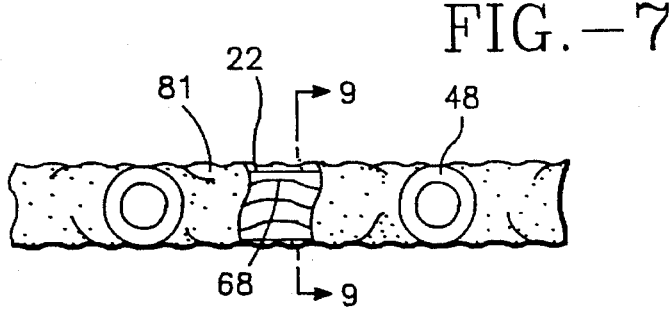
FIG.—8
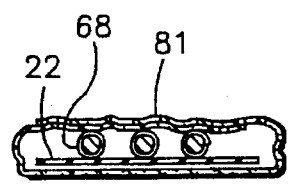
FIG.—9

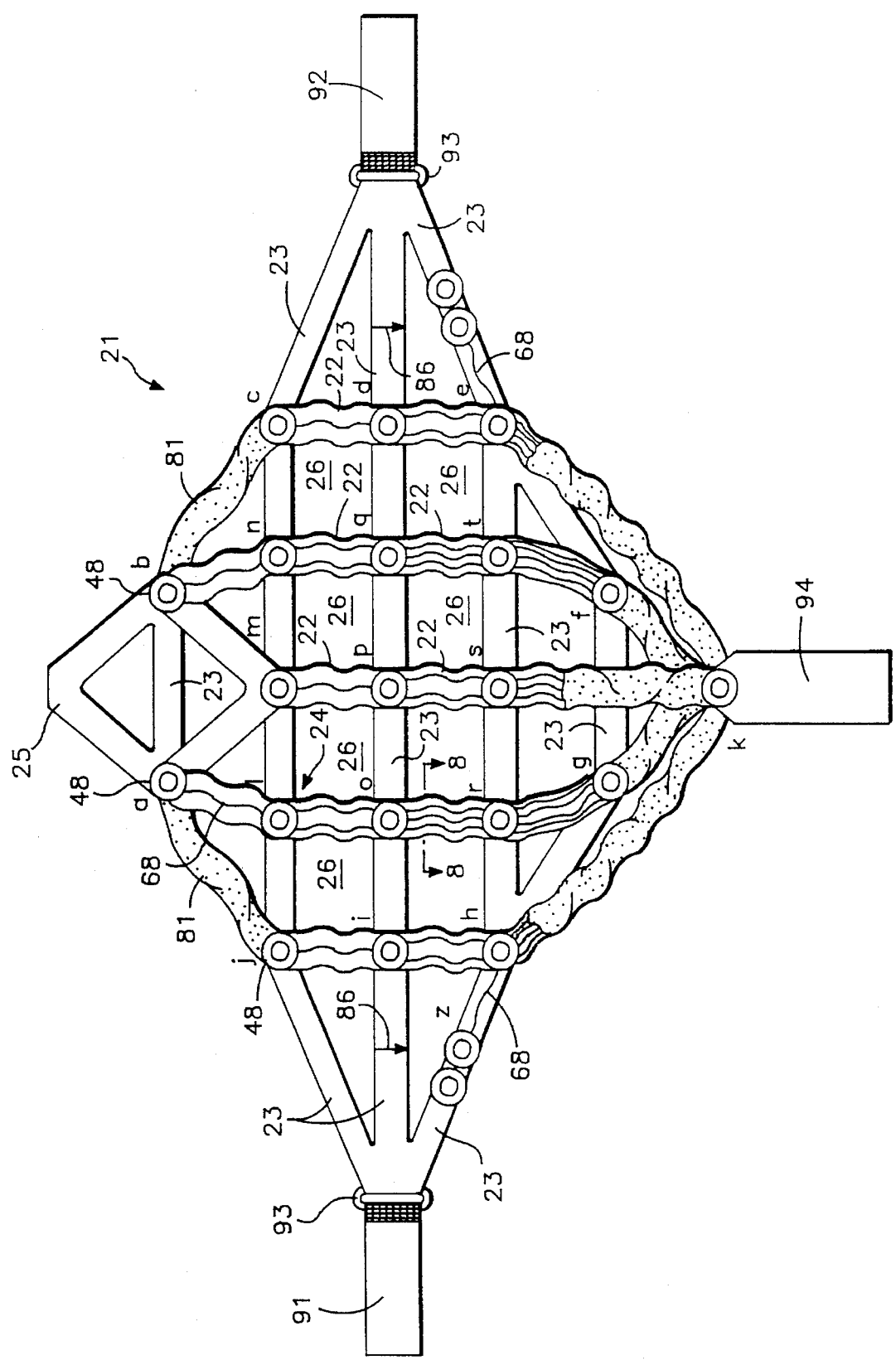
FIG.—6

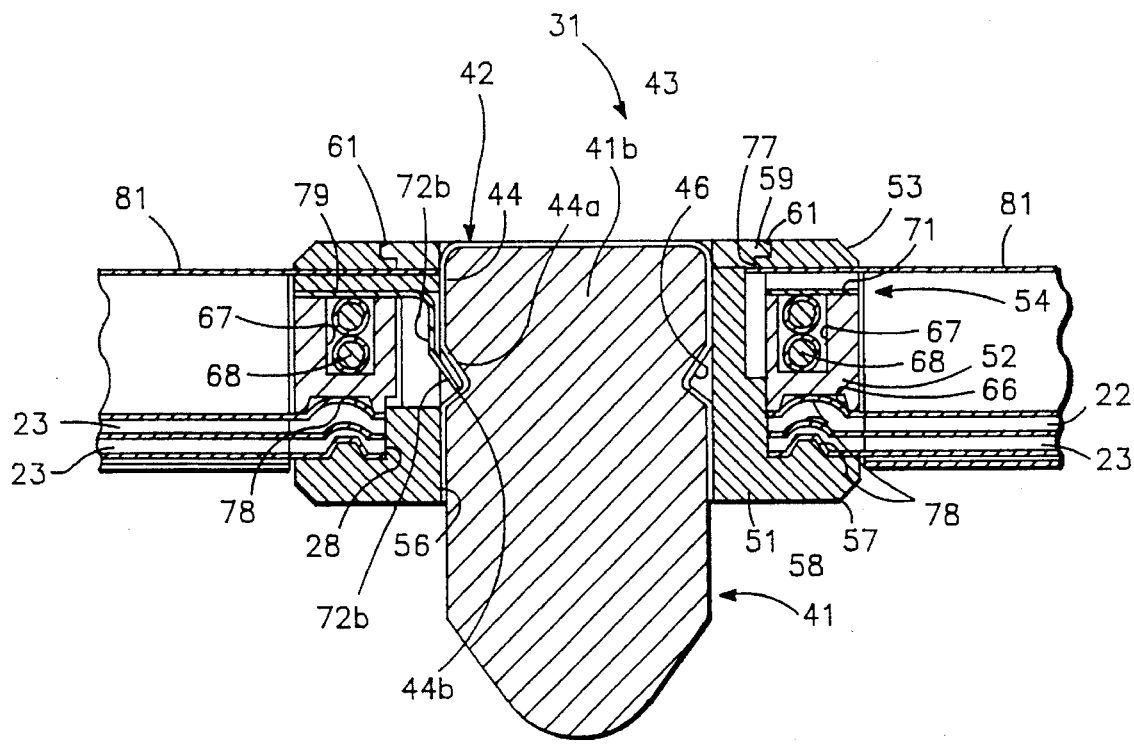
FIG.—10
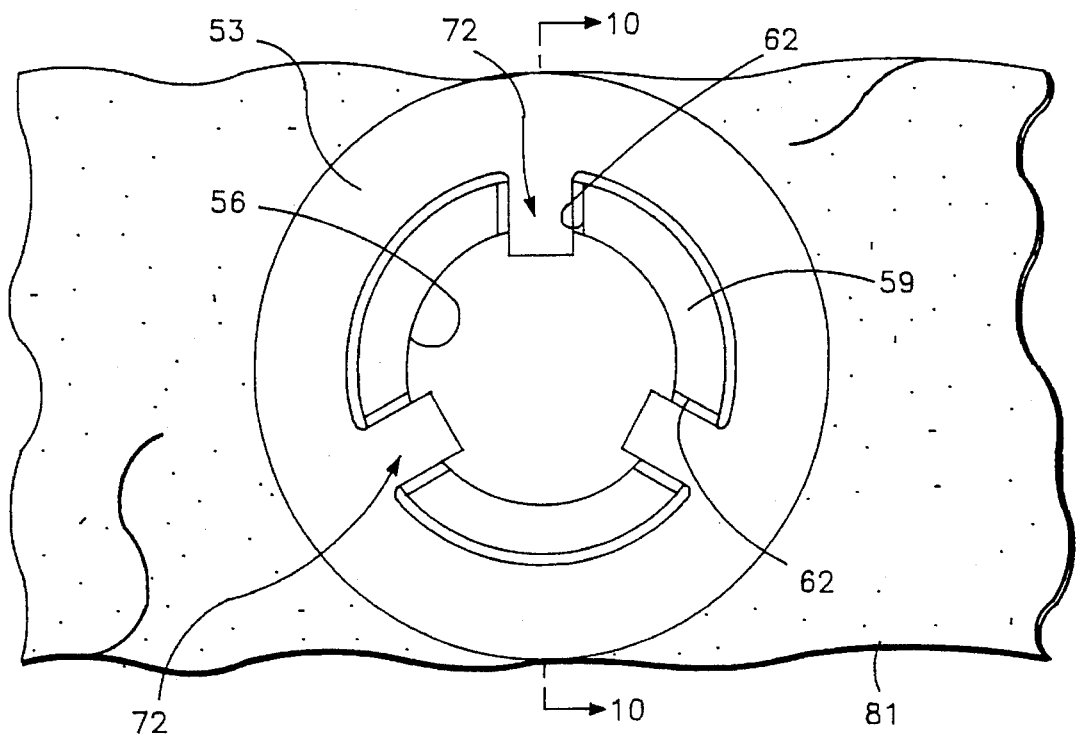
FIG.—11

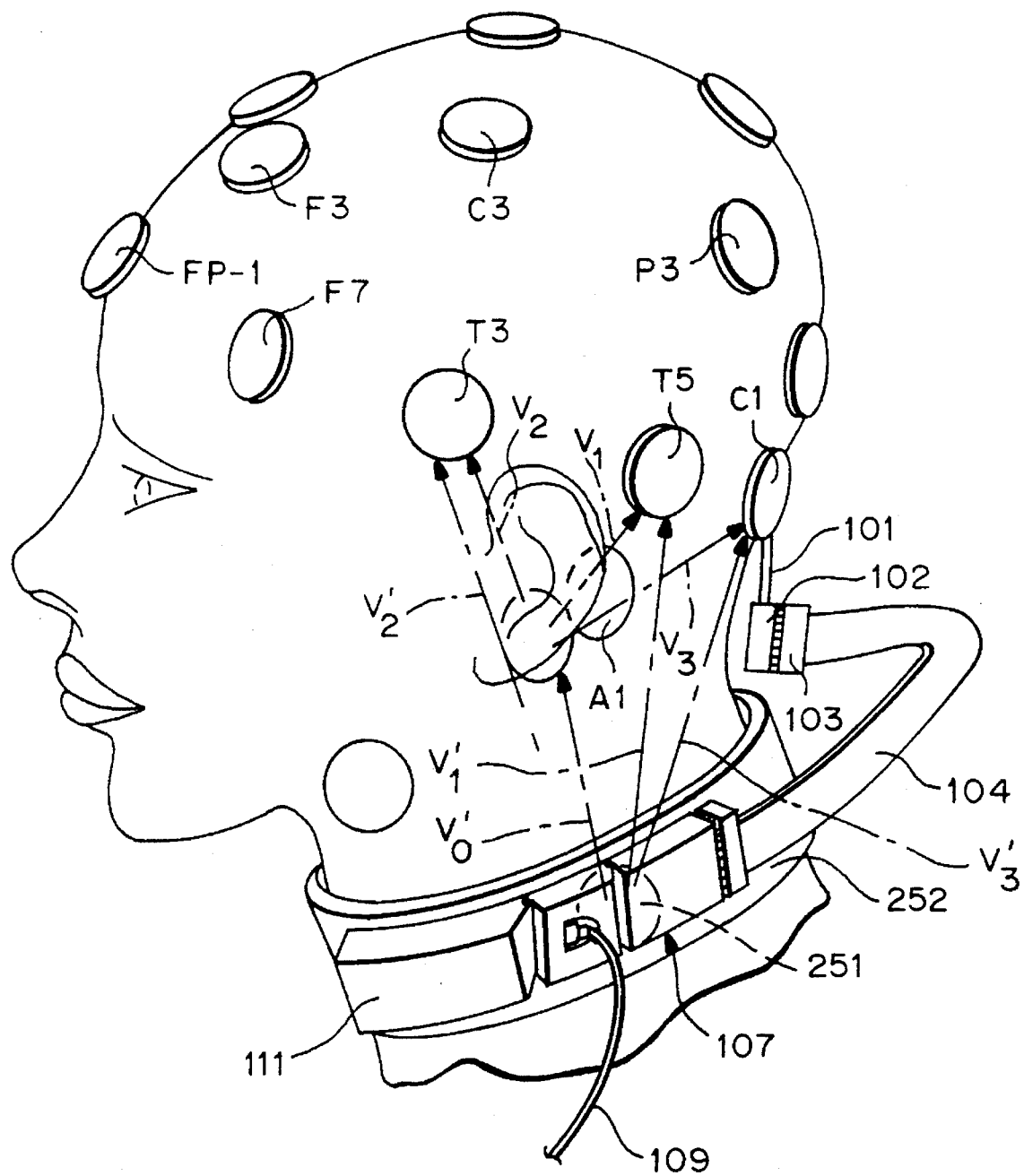
FIG.—16

EEG HEADPIECE WITH DISPOSABLE ELECTRODES AND APPARATUS AND SYSTEM AND METHOD FOR USE THEREWITH

This is a continuation of application Ser. No. 07/790,412 filed Nov. 8, 1991, now abandoned.

This invention relates to a headpiece with disposable electrodes and apparatus and system and method for use therewith and more particularly to such a headpiece, apparatus, system and method for making EEG measurements.

Heretofore, EEG measurements have been made on the heads of human patients utilizing various systems of electrode positions, as for example the international 10–20 system which is commonly used. In the past, these electrode positions have been charted on the head of the patient by marking the positions in an appropriate manner with reference to the nasion, inion and the preauricular points. The electrode positions on the head utilizing the 10–20 system are marked with a grease pencil which takes approximately 15–20 minutes of time because the technician is using a tape measure for measuring the electrode positions. The electrode positions on the head of the patient are then cleaned with a cotton swab or ground up pumice stone or some other abrasive to provide a good electrical contact to a conducting filler in a gold or silver-plated cup electrode. The cup electrode is either taped on or applied with collodion which when it dries solidifies and retains the electrode in the desired position on the head. Such a procedure requires between 30–45 minutes. Each of the electrodes is provided with wires which are typically 6'–10' long and are plugged into the console of the system for making EEG measurements. Thus a patient will have 21 wires going into the console. Often these electrodes will fall off the patient or fail to make good contact. Such systems have been very cumbersome because of the electrodes and the number of wires or conductors which are involved. They have also been very time consuming because of the patient preparation required. There is therefore a need for a new and improved EEG measurement apparatus, system and method which overcomes these disadvantages.

In general, it is an object of the present invention to provide a headpiece with electrodes thereon which are fastened on the headpiece in such a manner so that when the headpiece is positioned on the head of the patient, the electrodes are positioned in predetermined anatomical positions on the head of the patient regardless of the size of the head of the patient.

Another object of the invention is to provide a headpiece of the above character in which a tape measure is not required for positioning the headpiece because of the preauricular nasion and inion marks provided on the headpiece.

Another object of the invention is to provide a headpiece of the above character which utilizes disposable electrodes.

Another object of the invention is to provide a headpiece in which strips are formed of an elastic material for carrying the electrodes.

Another object of the invention is to provide a headpiece of the above character in which the elastic strips are secured to each other by the use of snap fasteners eliminating the need for stitching.

Another object of the invention is to provide a headpiece of the above character which provides open spaces between the elastic strips to facilitate movement of hair from under the electrodes.

Another object of the invention is to provide a headpiece of the above character in which the portion of the electronics associated with the headpiece is provided in modules separate from the headpiece.

Another object of the invention is to provide a headpiece of the above character in which extendable conductors are associated with certain of the elastic strips for connection of the electrodes to the electronics modules.

Another object of the invention is to provide a headpiece of the above character in which protective coverings are provided over the extendable conductors and the elastic strips associated with the same.

Another object of the invention is to provide a headpiece, apparatus, system and method in which a single cable utilized for carrying the signals away from the electronics modules.

Another object of the invention is to provide a headpiece, apparatus, system and method which facilitates the use of radio frequencies or optical telemetry.

Another object of the invention is to provide a headpiece, apparatus, system and method which is relatively lightweight and compact and which permits the patient to freely move about.

Additional objects and features of the invention will appear from the following description in which the preferred embodiments are set forth in detail in conjunction with the accompanying drawings.

FIG. 5 is a rear elevational view of the headpiece shown in FIGS. 1, 2, 3 and 4.

FIG. 6 is a plan view of the headpiece shown in FIGS. 1–5 before placement on the head of a human being.

FIG. 7 is a view showing a portion of the headpiece shown in FIG. 6 showing the protective covering before it is wrapped about the elastic strips of material.

FIG. 8 is a cross-sectional view similar to FIG. 7 taken along the line 8—8 of FIG. 6 but showing the protective covering wrapped about the elastic strips.

FIG. 9 is a cross-sectional view taken along the line 9—9 of FIG. 8.

FIG. 10 is a cross-sectional view of one of the electrode assemblies shown in FIGS. 1–5 taken along the line 10—10 of FIG. 11.

FIG. 11 is a top plan view of the electrode assembly shown in FIG. 10 looking along the line 11—11 of FIG. 10 with the electrode removed.

FIG. 16 is a schematic diagram showing the manner in which equivalent voltages are obtained for an EEG using a reference in the neckband rather than ear lobe references.

Figure 1:
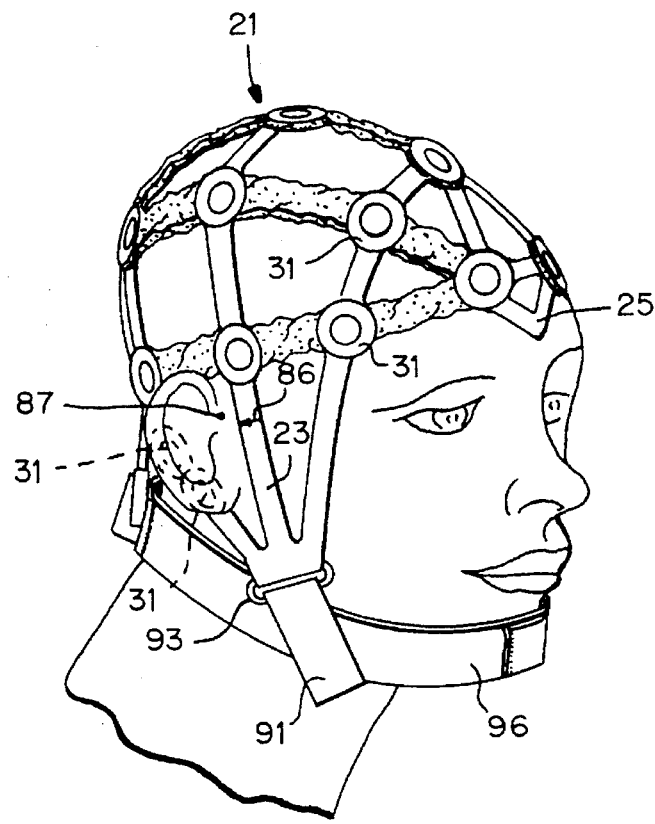
FIG. 1 is a side elevational view of the right side of a headpiece mounted on a model of a human being with the associated neckband.

In general, the headpiece for making EEG measurements on the head of a human patient utilizes an electrode positioning system requiring the use of a plurality of electrodes in predetermined anatomical positions on the head of the human patient. The headpiece is comprised of a plurality of strips of elastic material forming a pattern. A plurality of electrodes are mounted in spaced apart positions on these strips of elastic material. Means is connected to the strips and is adapted to secure the pattern of strips to the head of the patient by stretching of the strips so that the electrodes are positioned in the desired anatomical positions regardless of the size of the head of the patient.

More in particular, the EEG headpiece 21 consists of a plurality of strips 22 and 23 formed of an elastic material to form a criss-cross pattern 24 (see FIG. 6). The strips 22 extend longitudinally, i.e., from front to back of the head, whereas the strips 23 extend transversely in directions which cross over the strips 22 to form the pattern 24. This pattern 24 of strips 22 and 23 of elastic material can be formed in a suitable manner, as for example, from a flat sheet of latex which can range in thickness from 0.006" to 0.025" with a preferable thickness being approximately being 0.010".

As shown in FIG. 6, the pattern 24 includes a vee-shaped portion 25 and can be formed from a flat generally rectangular sheet of latex which is die cut to provide the strips 22 and 23 to form the generally rectangular openings or spaces 26 between the strips 22 and 23. Thus, in the pattern 24 shown in FIG. 6 there have been provided five longitudinally extending strips 22 and five transversely extending strips 23. A plurality of junctions 27 having holes 28 therein are provided for receiving electrode assemblies 31 as hereinafter described. These junctions 27 are generally circular in conformation and are provided in predetermined positions in the pattern 24 at crossover areas of the strips 22 and 23.

The junctions 27 are located so that the electrode assemblies 31 mounted therein are positioned in accordance with the desired electrode positions as for example the international 10–20 system, which is commonly used. The junctions 27 so positioned have been identified with the letters of the alphabet a–x. Additional electrode assemblies 31 have been located at locations y and z, adjacent location e and h. The two electrode assemblies at location y can be used as a ground reference with redundancy. The two electrode assemblies 31 at location z can be used as inputs or an alternative reference as desired.

The construction of the electrode assemblies 31 is shown in FIGS. 10 and 11. As shown therein each electrode assembly 31 consists of a cylindrical electrode 41 which is formed of a material of the type described in application Ser. No. 07/582,749, filed Sep. 14, 1990, now U.S. Pat. No. 5,211,174, and in continuation-in-part application Ser. No. 07/745,863 filed Aug. 16, 1991 now U.S. Pat. No. 5,331, 959. The cylindrical electrode 41 is provided with a cone-like tip 41a. The base portion 41b of the electrode 41 is placed in a deep-drawn cup-shaped container 42 which is provided with a planar top wall 43 and a cylindrical side wall 44 extending at right angles thereto. The cylindrical side wall 44 extends approximately one half the length of the electrode 41. An annular recess or groove 46 is formed in the side wall of 44 intermediate the ends of the same. The recess 46 is formed by a downwardly and inwardly inclined side wall portion 44a and an outwardly extending portion 44b extending at an angle of approximately 55° thereto.

The electrode assembly 31 also includes an electrode holder 48. The electrode holder 48 consists of three plastic parts 51, 52 and 53 and a metal spring part 54. The part 51 is in the form of a flanged barrel which has a centrally disposed hole 56 therein. It is provided with diametrically extending rim 57 which has an annular raised protrusion 58 formed thereon. The upper portion of the barrel-shaped part 51 is provided with a shoulder 59 which has a chamfer 61 formed thereon. The barrel-shaped part 51 is also provided with three recesses 62 which are spaced 120° apart for a purpose hereinafter described. The part 52 has a ring-like configuration and is provided with an annular recess 66 on the lower extremity thereof which is adapted to overlie the annular protrusion 58 for a purpose hereinafter described. It is also provided with U-shaped recesses 67 on opposite sides of the barrel part 51 extending tangentially with respect thereto. The recesses 67 are adapted to receive a plurality of insulated conductors 68, as for example the two conductors 68 in each recess 67. The annular metal spring part 54 is formed with an annulus 71, that overlies the recesses 67 in the part 52 and the conductors 68 disposed therein. The annulus 71 is provided with downwardly turned tabs 72 which have portions 72a extending inwardly at an angle with respect to vertically depending portions 72b. The tabs 72 extend into the recesses 62 and are adapted to engage the recess 46 of the container 42 of the electrode 41 when it is positioned within the hole 56 to establish electrical contact between the part 54 and the electrode 41. Thus when a container 42 carrying the electrode 41 is positioned within the hole 56, the container 42 carrying the electrode 41 is positioned within the hole 56 and is forced inwardly until the tabs 72 snap into and are seated within the annular recess 46. This ensures that the electrode assembly 31 will not be pushed out of the electrode holder 48 when the head piece 21 is placed on the head of the human being as hereinafter described.

The part 53 is in the form of a snap ring which is provided with a centrally disposed hole 76 and is snapped over the shoulder 59 by engaging the chamfer 61 to yieldably urge the ring 53 over the shoulder 59. When the lip 77 formed on the ring 53 snaps under the shoulder 59 the snap ring 53 is retained in engagement with the barrel-shaped part 51. At the same time the snap ring 53 serves to clamp the inner margins of the strips 22 and 23 defining the holes 28 between the part 52 and the flange or rim 57 of the part 51 so that the electrode holder 48 is firmly clamped in place. In order to ensure that the latex strips 22 and 23 are not pulled out from the electrode holders 48, washers 78 formed of an abrasive paper are positioned between the strips 22 and 23 and the parts 51 and 52 to firmly grip the inner margins of the strips 22 and 23 surrounding the holes 28.

One of the leads or conductors 68 is connected to the metal snap ring 54 as for example by the use of solder 79 establishing a conducting path from the conductor 68 to the annulus 71 of the snap ring 54 (see FIG. 10). Thus it can be seen that the electrode holders 48 serve as snap fasteners for interconnecting the plastic strips 22 and 23 to form the headpiece 21 and thereby eliminating the need for stitching or other types of fastenings.

As shown in FIG. 6, the conductors or leads 68 are connected to each of the electrode holders 48 provided at the junctions 27 which extend from the front to the rear of the headpiece 21. Thus by way of example there is one conductor 68 extending from the electrode holder 48 at the junction b to the electrode holder 48 at junction n and there are two conductors 68 extending from the electrode holder 48 at junction n to junction q, three conductors 68 from the electrode holder 48 at junction q to junction t, four conductors 68 extending from the junction t to junction f and five conductors 68 extending from junction f to junction k. Similarly there is one conductor 68 extending from the electrode holder 48 at junction m to junction p, two conductors 68 from junction p to junction s and three conductors

68 extending from junction s to junction k. Other conductors 68 are provided where needed as shown in FIG. 6 to bring all of the outputs of the electrode assemblies 31 to the junction k.

With conductors 68 of five different lengths, it is possible to make connections to all of the electrode holders 48 of the electrode assemblies 31 positioned on the junctions 27. The conductors or wires 68 have a length which is substantially greater than that of the length of the elastic strip between the junctions to accommodate the stretching which, when the headpiece 21 is mounted on the head of a patient, occurs in the strips between the junctions. Although the latex sheet material which is utilized in the present invention is capable of stretching up to 800%, the stretching which is required to accommodate the full range of human head sizes is in the range of 22–25%. Thus, to be sure that the wires or conductors 68 are long enough to accommodate such stretching, the wires 68 can be made in lengths which are 25–30% greater than the length of the elastic strips over which the conductors 68 are disposed.

Protective sleeves 81 are provided on certain of the latex strips 22 and 23 which extend between the junctions 27. These sleeves 81 are provided for two purposes. First to enclose the wires or conductors 68 which extend from the electrode assemblies 31 and second to prevent the latex strips from grasping the patient's hair as the headpiece 21 is placed on the head of the patient or removed from the head of the patient. These sleeves 81 can be formed of suitable material such as Nylon or a polyester fabric. The fabric is cut in lengths corresponding to the lengths of the strips 22 and 23. Cutouts 82 are provided at the locations of the electrical holders 48. The fabric is then folded over and sealed to itself by suitable means such as an adhesive as shown in FIGS. 8 and 9 to enclose the strip 22 and the conductors 68. These sleeves 81 are flexible and have a length greater than the leads 68 to permit stretching of the strips 22 and 23 when the headpiece 21 is positioned on the head of a human being. The sleeves 81 have their top sides clamped in between the part 53 and the part 52 of each of the electrode holders 48. When the elastic strips 22 and 23 are relaxed, not stretched, the sleeves will be gathered with folds in them to accommodate the decreased lengths of the strips 22 and 23.

Figure 2:
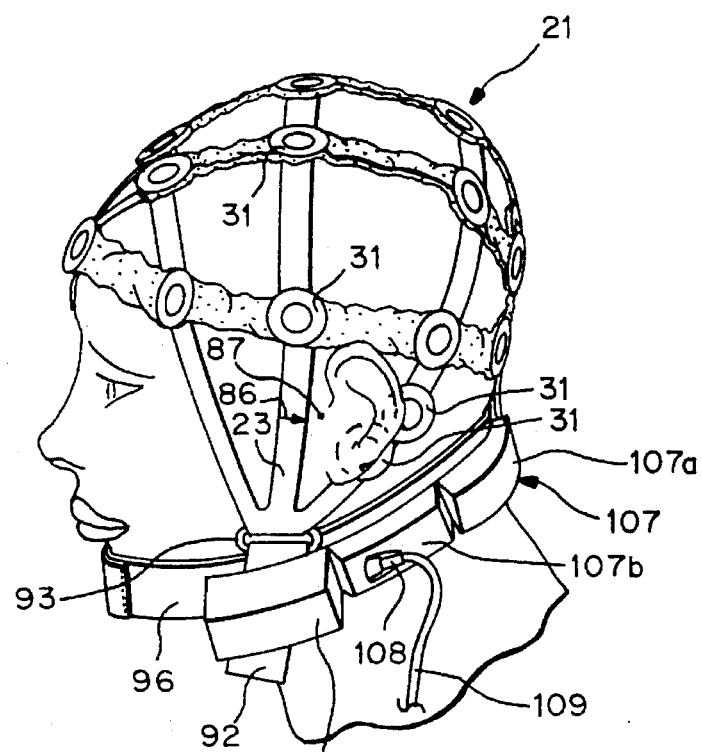
FIG. 2 is a left-side view of the headpiece shown in FIG. 1 but showing the electronics modules with a battery pack mounted on the neckband and the output cable connected thereto.

First and second or a pair of preauricular marks 86 are provided on the headpiece 21 as shown in FIGS. 1, 2 and 6, to facilitate positioning of the headpiece 21 in the appropriate position on the head of the patient in alignment with preauricular points 87 adjacent the ears (see FIGS. 1 and 2) as hereinafter described.

Figure 3:
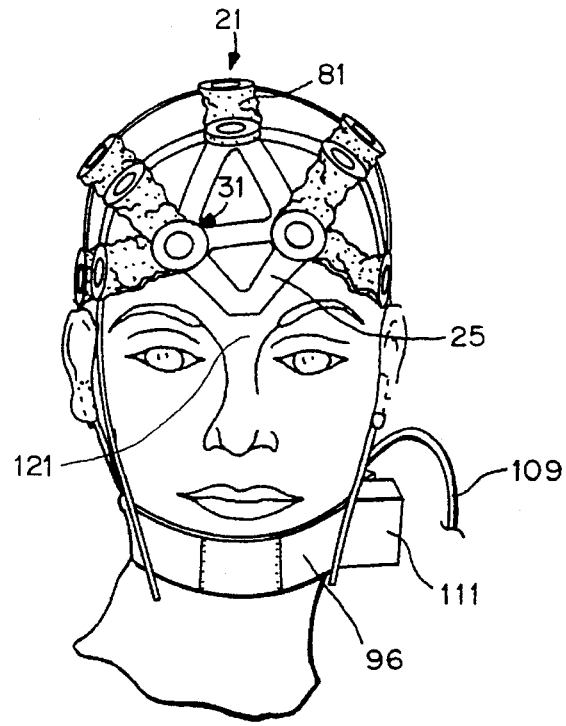
FIG. 3 is a front elevational view of the headpiece shown in FIGS. 1 and 2.
Figure 4:
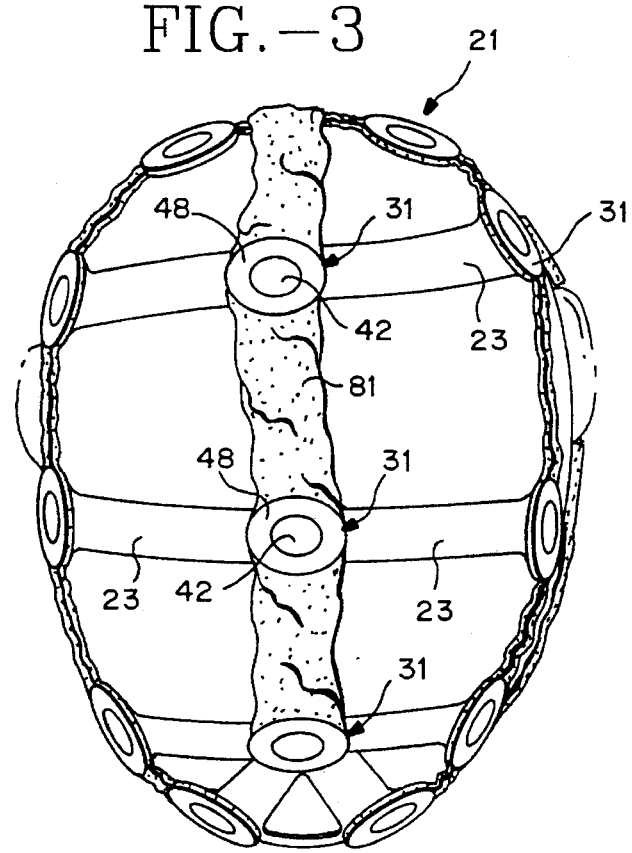
FIG. 4 is a top plan view of the headpiece shown in FIGS. 1, 2 and 3.

Straps 91 and 92 formed of a suitable material such as Velcro are provided on opposite sides of the headpiece 21 and extend through rings 93 secured to the elastic straps 23 as shown in FIG. 6. Another Velcro strap 94 is secured to the electrode holders 48 at the junction k. A Velcro neck band 96 is provided which extends about the upper neck of the patient and over the chin as shown in FIGS. 1, 2 and 3 to serve as anchoring means for the straps 91, 92 and 94 to hold the headpiece 21 in place. The neck band 96 can be adjusted to accommodate various sizes of necks.

The conductors 68 coming to the junction k are connected into a flat cable 101 which extends downwardly into a connector 102 which mates with another connector 103. The connector 103 is connected by a flat cable 104 to another connector 105 which mates with a connector 106 provided on an electronics module 107 formed into hinged sections 107a and 107b which is mounted on the exterior of the neck band 96 by suitable means such as Velcro. The module 107 is provided with an output connector 108 which is connected to a cable 109 which is adapted to be plugged into an interface box 110 utilized in connection with the headpiece as hereinafter described. A battery pack is provided as a part of the electronics module and 111 is mounted on the neckband 96 by Velcro adjacent the electronics module 107 to supply power to the electronics module 107.

In accordance with the 10–20 system, nineteen electrode assemblies 31 are provided. Two additional pairs of electrode assemblies 31 have been provided at the locations y and z so that when the headpiece 21 is mounted on the head of the patient they are disposed behind the earlobes on opposite sides of the head of the patient. In conventional systems, such electrodes are typically mounted on the ears of the patient and serve as reference electrodes. In the present embodiment of the invention these additional electrode assemblies 31 at locations y and z are treated as two additional EEG electrodes so that a total of twenty-one outputs are brought out from the electrode assemblies 31 to the electronics module 107.

Let it be assumed that it is desired to place the headpiece 21 onto the head of the patient in the form of an adult human being. The headpiece 21 is taken by two hands of the operator or attendant and stretched apart slightly and positioned on the head of the patient in such a manner that the preauricular marks 86 on the headpiece 21 are positioned on the preauricular points 87 of the ears of the patient and so that the other electrode assemblies 31 are positioned appropriately with respect to the nasion 121 (see FIG. 3) at the bridge of the nose of the patient and the inion 122 (see FIG. 5) at the beginning of the back of the neck of the patient. The positioning of headpiece 21 with respect to the nasion is facilitated by the vee-shaped portion 25 having its vee positioned at the nasion. The junction k of the headpiece 21 is positioned on or adjacent to the inion 122. The nasion 121 and the inion 122 and the preauricular points 87 serve as conventional reference points in the 10–20 system and are not electrode locations.

Because of the elasticity of the material utilized for the strips in the headpiece 21, it has been found that the electrode assemblies 31 are positioned in the proper positions with respect to these reference points regardless of the shape of the head and the size of the head. The elasticity of the headpiece makes it possible to readily accommodate different head shapes and sizes while still maintaining the electrode assemblies 31 in the desired positions necessary for the 10–20 system. The headpiece 21 can be designed to accommodate other proportional electrode positioning systems in the same manner as for the 10–20 system.

As soon as the headpiece 21 has been properly positioned on the head, the Velcro straps 91 and 92 can be secured to the neck band 96 placed on the patient to hold it in place and similarly the Velcro strip 94 also can be secured to the neck band 96.

As soon as the headpiece 21 has been properly positioned, one can see the person's scalp or hair through the holes 56 provided in the electrode holders 48. If an electrode holder 48 is sitting on hair on the head of the person, the electrode holder can be lifted by one hand of the operator and the fingers of the other hand can be inserted into the openings 26 between the elastic strips 22 and 23 to separate the hair underneath the electrode holder so that when the electrode holder 48 is released it sits directly on the scalp of the patient. A cotton swab or similar device can then be inserted through the holes 56 to clean off any surface oils. As soon as this has been accomplished, the electrodes 41 which are disposed in the containers 42 can be positioned in the holes 56 so that the conductive polymer comes into engagement with the scalp of the patient and with the spring metal tabs 72 seated in the annular recess of the electrode containers 42 so that the planar surface 43 of the container 42 is in alignment with the top surface of the plastic snap ring 53. The three tabs or metal clips 72 serve to ensure that the container 42 is properly seated within the electrode holder 48 and make sure that the conductive polymer electrodes 41 make excellent contact with the scalp of the patient. In positioning the electrodes 41 with the electrode holder 48, the operator can feel and hear a click when the tabs 72 enter the recess 46. The elastic strips 22 and 23 forming a part of the headpiece 21 serve to yieldably retain the conductive polymer electrodes 41 in contact with the scalp of the patient. Once the retainer has been snapped into position, it cannot be retracted except in the direction in which it entered the electrode holder 48. It only can be pushed forwardly when it is desired to remove the electrode after the EEG measurements hereinafter described have been made.

Figure 15A:
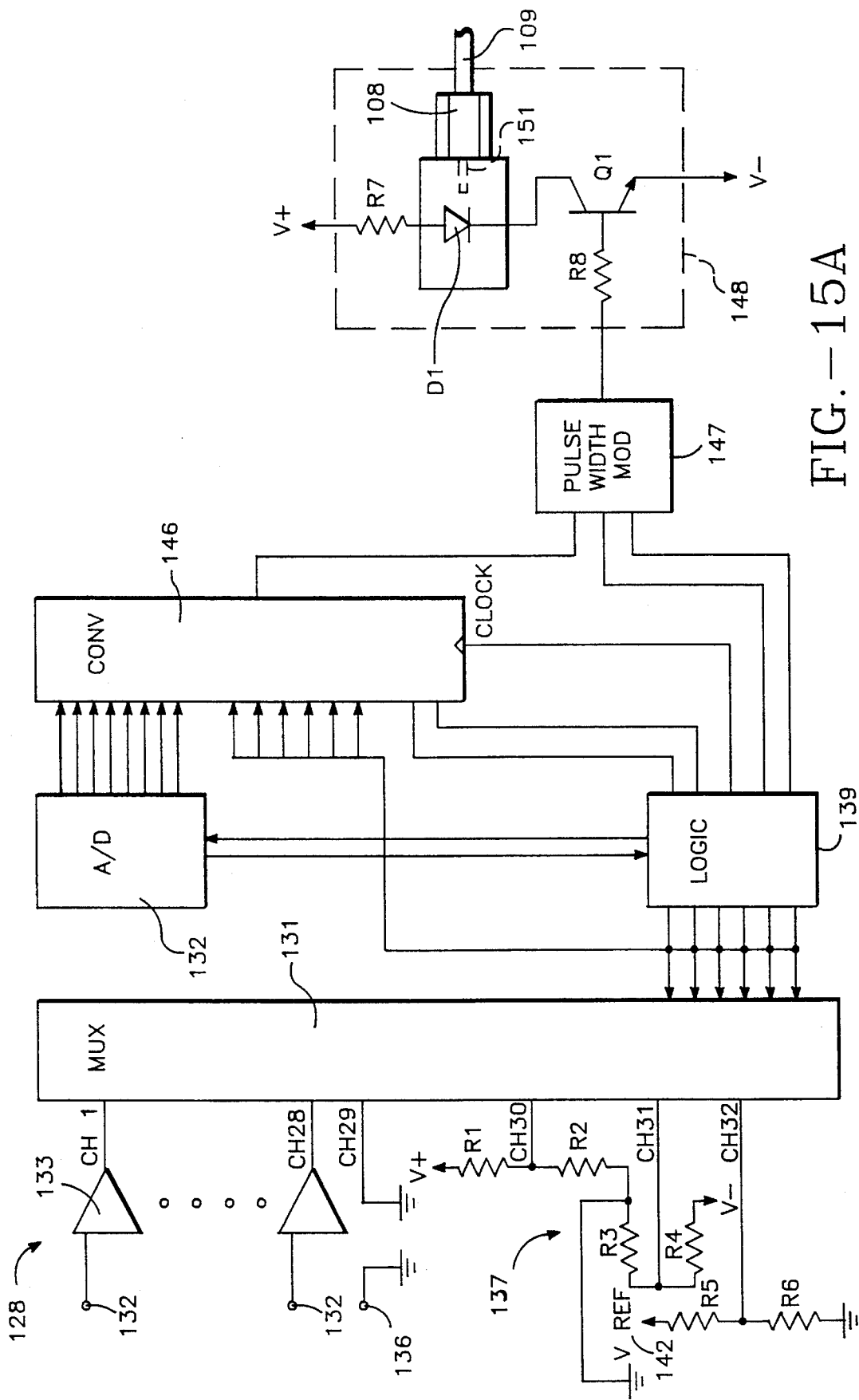
FIGS. 15A, 15B and 15C are block diagrams showing the electronic circuitry utilized in the apparatus and system of the present invention.

After the headpiece 21 has been mounted upon the head of the patient and after the electrodes 41 have been positioned therein, the fiber optic cable 109 can be connected to the interface box 110. The electronics module 107 carries transmitter circuitry 128 which is shown in FIG. 15A and the interface box 110 carries the receiver circuitry 129 shown in FIG. 15B. The transmitting unit includes a 32-channel multiplexer 131 which transmits EEG inputs 132 supplied by the electrodes 31 over the cable 109. The inputs 132 are connected through amplifiers 133 to channels 1–28. Twenty-eight of such channels are provided even though in the present 10–20 system, only 21 channels are required. The output from the selected reference electrode is supplied to an input 136 which is connected to a circuit ground as shown. Channel 29 similarly is connected to circuit ground. Additional channels 30, 31 and 32 are provided in the multiplexer 131. Channels 30 and 31 are connected to a resistive network 137, comprised of resistors R1, R2, R3 and R4, connected to V+ at one end and V− at the other end. The voltages of the batteries represented by the V+ and V− are divided down so as to be within the range of the A-D converter 138 receiving the output of the multiplexer. The junction between resistors R2 and R3 is connected to circuit ground as shown. Channel 30 is connected between resistors R1 and R2 and channel 31 is connected to the junction between resistors R3 and R4. The voltage supplied to the V+ and V− terminals respectively would be approximately to 1 to 1.2 volts positive and 1 to 1.2 volts negative. The channels 30 and 31 serve to provide divided down battery voltages which can be utilized in the demultiplexer hereinafter described to ascertain the condition of the batteries and whether or not they should be replaced. By transmitting this information to A-D converter 138 the battery circuitry hereinafter described provided in the receiving unit 129 can be utilized for detecting low batteries eliminating a need for such circuitry in the transmitting unit which is located in the electronics module 107.

Channel 32 receives the output from a resistive network 141 comprised of resistors R5 and R6. The R5 resistor is connected to a fixed voltage reference 142 whereas the resistor R6 is connected to circuit ground. This reference provided on channel 32 is utilized to adjust the gain of the D/A converter hereinafter described provided in the receiver circuitry 129. The A/D converter 138 is of a conventional type and is under the control of a logic unit 139 and provides its output to a parallel-to-serial converter 146. The output of the converter 146 is supplied to a pulse width modulator 147. The pulse width modulator 147 supplies its output to an energy converter 148 which converts the output of the pulse width modulator 147 to a different energy as for example radio frequency energy, infrared energy or optical energy. In order to reduce interference and noise problems, it has been found preferable to utilize optical energy or infrared energy. Thus, a light emitting diode D1 is provided which is coupled to a V+ voltage through a resistor R7. The output of the pulse width modulator 147 is connected through a current limiting resistor R8 to the transistor Q1 so that the transistor Q1 in combination with the resistor R7 determine the current flow through the diode D1. The transistor Q1 is connected to a minus voltage source, as indicated. The light emitted by the diode D1 which switches very rapidly is picked up by a fiber optics bundle 151 and is connected to a connector 108 hereinbefore described. The connector 108 is connected to one end of the fiber optic cable 109 which extends from the transmitter circuitry 128 in the headpiece 21 to the receiver circuitry 129 in the interface module 110. The fiber optic cable 109 has another connector 152 on its other end mounted in a receptacle 153. The receptacle 153 is mounted in an energy converter 154. The connector 153 is provided with a fiber optic bundle 156 which supplies its light output to a photosensitive transistor Q2 that is turned on and off by the data being supplied by the light energy being emitted from the fiber optic 156. The transistor Q2 is connected between ground and a V+ voltage through a resistor R9. The output of the transistor Q2 which is pulse width modulated is supplied to an inverter D2 that supplies a pulse width modulated signal to a serial-to-parallel converter 157. The serial-to-parallel converter 157 supplies its parallel outputs to a D/A converter 158. The output of the D/A converter 158 is supplied to a demultiplexer 159. The serial-to-parallel converter 157 also supplies channel information through a that 161 which supplies channel select latch information to the demultiplexer 159. The outputs of the demultiplexer 159 are supplied to a sample-and-hold circuit 162 for each of the channels which include a capacitor connected to ground with the capacitors being identified as C1–CN. The outputs of the capacitors are connected to operational amplifiers which are identified as A1–A11. The outputs of the amplifiers are supplied on outputs 163 to provide EEG outputs for each of the channels.

Thus, the output on the channels 1–28 from the terminals 163 would be identical to the EEG inputs 132 multiplied by the appropriate gain of the system. The outputs of channels 29, 30 and 31 are reconstructed with similar sample-and-hold circuits 162. The reconstructed signals are supplied to a low battery voltage detect circuit 166 which supplies a signal to a low battery indicator 167 comprised of a current limiting resistor R10 connected to the base of a transistor Q3. The emitter and collector of the transmitter Q3 are connected between ground and a resistor R11 which is connected through a light emitting diode D3 to V+. When a low battery condition is sensed, the light emitting diode D3 is operated to give a visual indication. Thus, it can be seen that the transistor Q3 operates as an on/off switch so that diode D3 is turned on when a low battery condition is detected.

The channel 32 reference is recreated by another sample-and-hold circuit 162. The recreated reference is applied on a line 171 back to the D/A converter 158 so that the output from the D/A converter 158 is identical to that which has entered into the A/D converter 138. If it is desired to change the gain of the system as for example to increase the gain of all channels by 20%, this can be readily accomplished by changing the reference voltage to the D/A converter 158 by adjustment of the knob 172 on the interface box 110.

In the sample-and-hold circuits 162, the storage capacitor for each channel, as for example C1 for channel 1, is sampled for very short periods of time, as for example, once every millisecond. The capacitor holds the charge which is supplied to the high impedance operational amplifier, as for example A1 for channel 1, so that the output from the operational amplifier follows the voltage on the sample and hold capacitor.

A logic controller or microprocessor 173 is provided with an output to the serial-to-parallel converter 157 and has an output connected to the latch circuit 161. It also has an input which is supplied from the invertor D2 of the energy converter 158 which is also supplied to a one-shot multivibrator 174 to the serial to parallel converter 157. The one-shot is used to reconstruct the clock signal necessary to shift the data into the serial to parallel converter 157.

Figure 14:
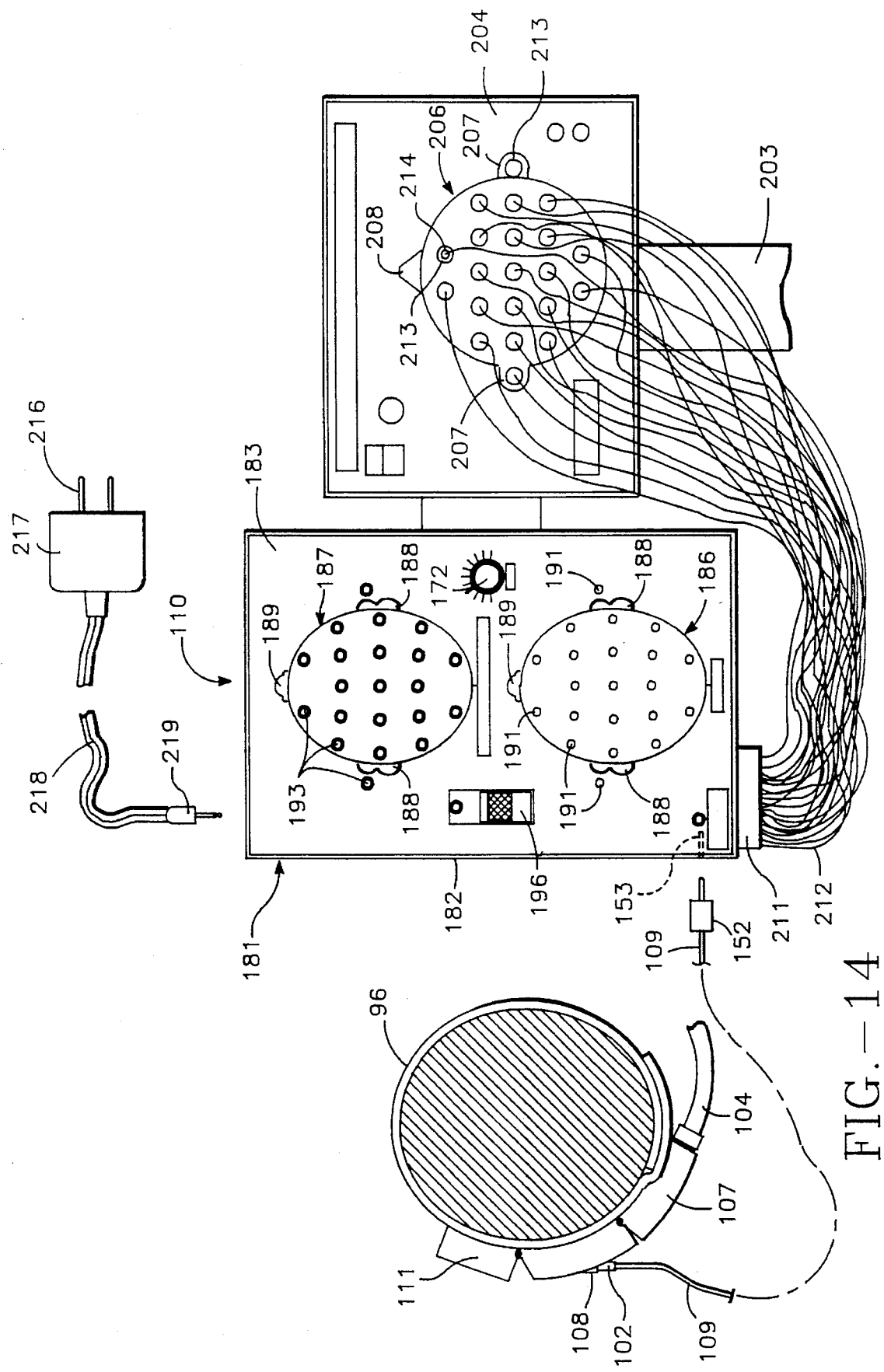
FIG. 14 is a front elevational view of the demultiplexer interface box connected to and mounted on the pedestal of a conventional EEG apparatus.
Figure 15B:
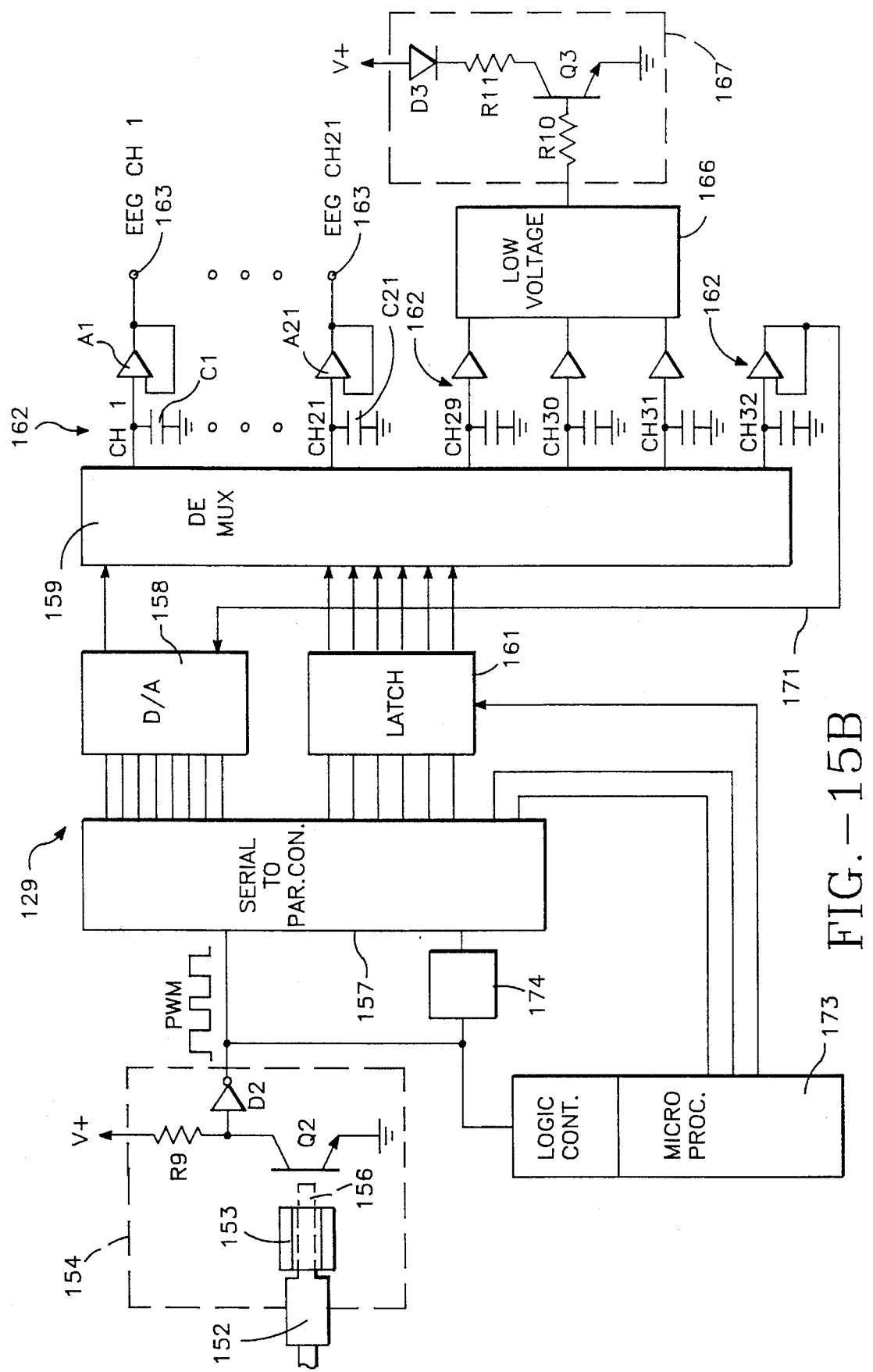

The circuitry shown in the block diagram in FIG. 15B is provided within the interface box 110 (see FIG. 14) which is provided with a rectangular box-like case 182 which is provided with a planar headboard 183 mounted therein. The headboard 183 has two diagrammatic representations 186 and 187 of heads each of which is provided with a pair of ears 188 and a nose 189 oriented in the same direction on each representation. The head representation 186 is provided with a plurality of sockets 191 which are positioned on the head representation in accordance with the 10–20 international system. Similarly, the head representation 187 is provided with a plurality of indicators 193 in the form of light emitting diodes also positioned on the head representation 187 in accordance with the 10–20 international system. These indicators are appropriately labeled. An on-off power switch 196 is provided on the headboard 183.

The case 182 is mounted by bracket to a console 201 that is mounted on a pedestal 203 which forms a part of a conventional EEG apparatus, the remainder of which is not shown. The console 202 is provided with a headboard 204 which is provided with a head representation 206 having ears 207 and a nose 208 oriented in the same direction as the head representations 186 and 187 on the interface box 110.

The outputs 163 from the circuitry shown in FIG. 15B are connected to the appropriate terminals 191 of the head 186. They are also connected to a connector 211 removably secured to the interface box 110 and are connected by a plurality of leads 212 connected to plugs 213 which are fitted into sockets 214 provided in the head 206. The sockets 214 are also arranged in accordance with the 10–20 international system. Alternatively, it should be appreciated that conductors and wires not shown also can be provided which have plugs in each end with the plugs in one end being capable of being seated within the sockets 191 of the head 186 and the other ends carrying plugs to be seated in the sockets 214.

By making the connections in this manner to the console 202 of conventional EEG apparatus by plugging into the terminals 214 provided in the head representation 206, the conventional EEG apparatus assumes that it is receiving electrical signals directly from the head of the patient rather than being supplied through the apparatus of the present invention which in fact is the case. It is for this reason that the 10–20 international system has been utilized on the head representations 186 and 187 as well as the head representation 206 so that the outputs 163 received from the head of the patient will be fed to the corresponding sockets 214 of the head representation 206.

The interface box 110 is provided with conventional power by the use of a plug 216 mounted on a nine volt transformer 217 to provide a nine-volt power supply on the cord 218 which is supplied to a plug 219 that is to be plugged into the case 182.

Figure 15C:
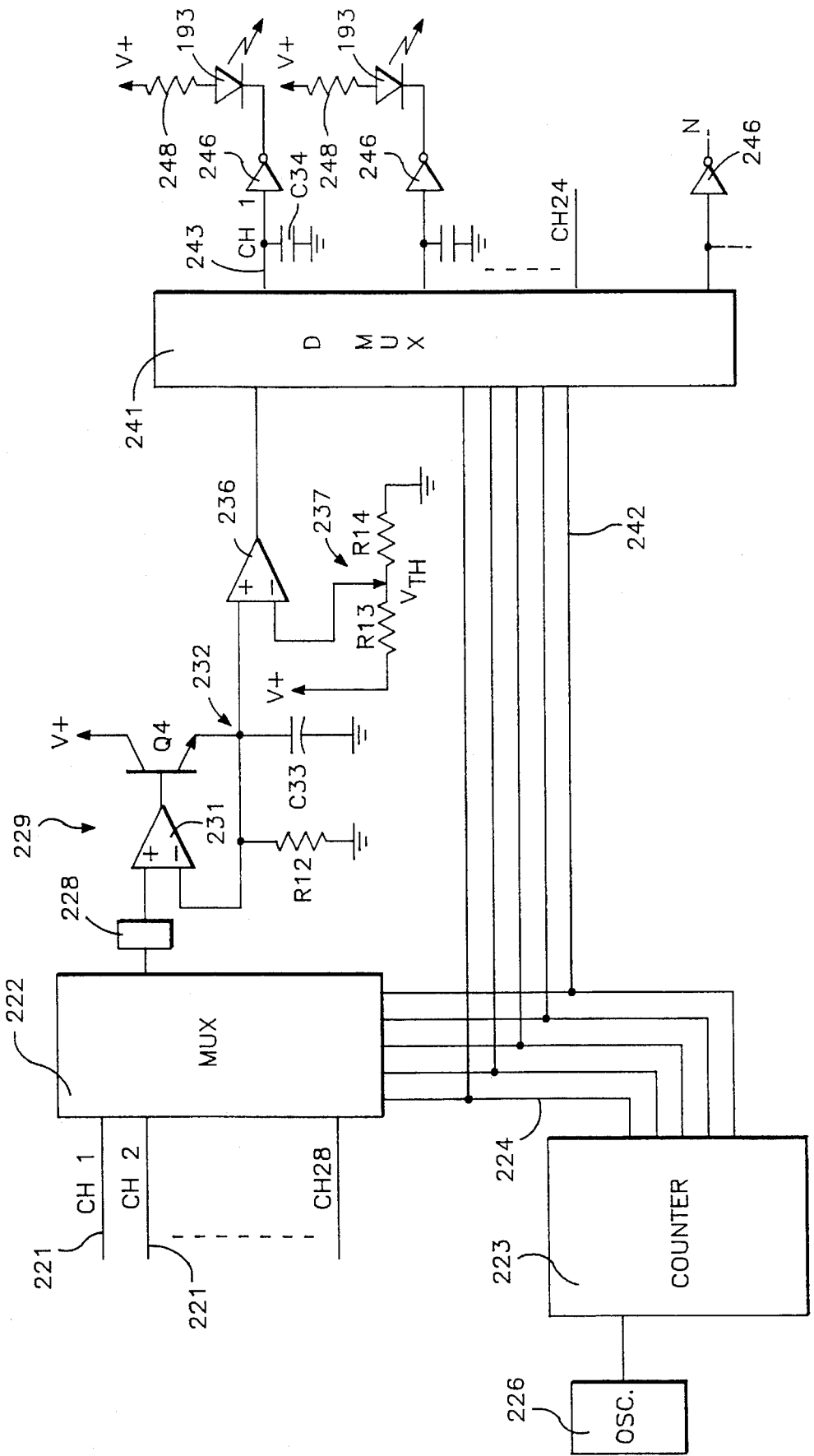

Additional circuitry is provided within the interface box 110 for detecting when there is an absence of an electrode 41 in the headpiece 21. This circuitry serves as means for detecting a high impedance contact between the electrode and the skin of a patient to indicate an unsatisfactory operating condition. This additional circuitry is shown in block diagram form in FIG. 15C. The outputs 163 from the head of the patient are connected to a plurality of inputs 221 which are connected into channels 1–28. The channels 1–28 are connected to an analog multiplexer 222 which is controlled by a counter 223 connected thereto by conductors 224. The counter 223 is controlled by an oscillator 226 which oscillates at a one hertz rate to advance the counter 223 at a one hertz rate. Because of the 28 inputs to the multiplexer 222, the connectors 224 provide five bits to provide the necessary combination for sampling the channels in the multiplexer 222. The output from the multiplexer 222 is supplied through a filter 228 which serves as a 60 hertz narrow band pass filter which will only pass the 60 hertz signals rather than the signals which are received from conventional EEG activity on the conductors 221. By only passing the 60 hertz signals it is assured that all that will be detected is the absence or presence of a high impedance condition. It should be appreciated that it may be unnecessary to utilize the filter 228 if there is sufficient amplitude difference between the conventional EEG signals and the 60 cycle noise signals.

The output from the filter 228 is supplied to a peak follower or rectifier 229. It consists of an operational amplifier 231 which supplies its output to the base of a transistor Q4. The collector of the transistor Q4 is connected to a positive voltage V+ and the emitter is connected to a network 232 consisting of a capacitor C33 and a resistor R12 connected to ground and connected to the other input of the operational amplifier 231. The output from the peak follower or rectifier 229 is supplied to a comparator 236 which is provided with a threshold voltage of $V_{TH}$ provided by a resistive divider network 237 consisting of resistors R13 and R14 with resistor R13 connected to V+ and resistor R14 connected to ground. The voltage threshold $V_{TH}$ is chosen to provide an output from the comparator 236 when a 60 cycle interference signal is received which indicates that an electrode is not present or there is a high impedance between the electrode and the skin of the patient. In other words, the comparator 236 detects a high 60 cycle content. A threshold voltage is provided on each channel 1–28 of the multiplexer 222 as it is advanced through the channels 1–28 by the counter 223.

The output from the comparator 236 is supplied to a demultiplexer 241 which is also provided with input leads 242 connected to the output leads 224 of the counter 223 so that it is advanced in the same way as the multiplexer 222 is advanced. When channel 1 is selected in the multiplexer 222, the corresponding channel 1 is selected in the demultiplexer 241. The outputs 243 for the channels 1–28 are connected to storage capacitors C34. The capacitors C34 are connected to ground as shown. The outputs 242 are also connected to buffer inverters 246 which are connected to light emitting diodes or indicators 193 which are connected to a V+ voltage through resistors 248. These indicators 193 are the ones provided in the head representation 187 (see FIG. 14). Thus it can be seen that if a strong 60 hertz signal is present by an indicator 193 being lit, this indicates that either no electrode is present or there is a very high impedance between the electrode and the skin. Thus a visual indication is given in the head representation 187 that an inadequate signal is being received by that electrode in that position on the head of the patient. This warns the operator to take appropriate steps to correct or remedy the situation which has been observed.

The use of shielded conductors 68 between the electrode holders 48 on the headpiece 21 and the electronics module 107 ensures that most if not all of the 60 cycle external noise is minimized if not totally eliminated. The body itself is an equipotential surface so that the electric field at any point on the body due to the 60 cycles present in the external fields is near or at zero.

Operation and use of the headpiece 21 with the associated electronics hereinbefore described can be used for making EEG measurements in a conventional manner. Let it be assumed that the headpiece has been positioned on the head of a patient in the manner shown in FIGS. 1–5. This can be readily accomplished by the operator taking the headpiece 21 in the two hands of the operator and stretching the elastic strips of the headpiece 21 and then positioning the same over the head of the patient in such a manner so that the preauricular marks 86 provided on the headpiece are aligned with the preauricular points 87 near the ears of the patient. At the same time, the front and back portions of the headpiece are positioned appropriately with respect to nasion 121 by use of the vee-shaped piece 25 and inion 122 using the k location. The electrode holders 48 are then checked to see whether any hair of the patient underlies the electrode assemblies 31. If that is the case, the appropriate electrode holder 48 is lifted with one hand and the hair is pulled aside from underneath the electrode holder 48 by inserting the other hand through a space 26 provided between the elastic strips 22 and 23 of the headpiece 21. Thereafter, if desired, a Q-tip or other instrument with a cotton swab can be inserted through the hole 56 to swab the surface of the skin underlying the electrode holder 48. Thereafter, the electrodes 41 which have been previously prepared and which have rounded points 41a in containers 42 are snapped into the electrode holders 48 in the manner hereinbefore described so that the rounded tip 41a of the electrode 41 engages the skin or scalp of the patient. This procedure is continued until all of the electrodes 41 have been snapped into position. The optical cable 109 is connected to the interface box 110. Appropriate connections are made from the interface box 110 to the console 202 by use of the connector 211 or alternatively by using leads connected from the sockets 191 in the head representation 186 on the headboard 183 to the corresponding sockets 214 in the head representation 206 in the console 202.

As soon as this has been accomplished, the power switch 196 on the interface box 110 can be turned on to place the apparatus in operation. The EEG measurements can thereafter be made in a conventional manner. As pointed out previously, the console 202 is supplied with EEG signals in the same manner as if the leads connected into the console 202 were connected directly to the head of the patient rather than through the apparatus of the present invention. This makes it unnecessary to modify existing EEG apparatus to utilize the apparatus of the present invention with its outstanding merits.

The head diagram shown in FIG. 16 shows the manner in which the apparatus of the present invention utilizing a reference 251 positioned within a Velcro neckband 252 serves the same function as an additional reference utilized by conventional EEG apparatus in which the reference is associated with one or both of the earlobes of the patient. In the present invention, the electrical activity in the brain of the patient can be measured with respect to the reference 251 in the neckband 252 while still obtaining the same end voltages as would be created by utilizing a reference positioned at the earlobe of the patient. This reference is identified as reference A1 and is disposed adjacent one ear of the patient while the other reference A2 (not shown) is disposed adjacent the other ear of the patient. The voltage between the reference 251 and the reference A1 is designated as $V_0'$. The voltage between the reference A1 and the electrode T5 is designated by an arrow $V_1$. The voltage between the reference 251 and the electrode D5 is designated by an arrow $V_1'$. The voltage between the reference A1 and the electrode T3 is designated by an arrow $V_2$ and the voltage between the reference 251 and the electrode T3 is designated as $V_2 2'$. Similarly, the voltage from the reference A1 to the electrode O1 is designated as $V_3$ and the voltage from the reference 251 to the electrode O1 is designated as the voltage $V_3'$.

From the foregoing, it can be seen that:

$$V_1 = V_1' - V_0'$$

$$V_2 = V_2' - V_0'$$

$$V_3 = V_3' - V_0'$$

In the same manner, the voltage $V_0'$ can be subtracted from the other voltages generated by the electrodes of the headpiece to provide voltages which are the same end voltages which would be achieved using an earlobe reference such as reference electrode A1 and/or the reference electrode A2.

In the apparatus of the present invention, the voltage signals are received by the demultiplexer 159. The demultiplexer 159 makes the calculations hereinbefore described to provide voltage information to the console 202 which in effect removes the changes in voltage which are created by the difference in positioning of the reference electrode 251 in the neckband 252 rather than the electrodes A1 and A2 normally associated with the earlobes of the patient.

With the use of a light weight optical cable 109, the patient can move around after the headpiece 21 is placed on the patient's head. Since the optical cable is very light weight, long lengths of the same can be utilized to give the patient freedom to walk about without disconnecting from the equipment if desired. Also, the optical cable 109 can be readily disconnected if desired. In addition, the optical cable 109 isolates the patient electrically from any danger from other external equipment since the headpiece is battery operated. This feature is particularly important during surgical procedures when electrically operated anesthesia monitors, cauterizing equipment and defibrillators are often used. By utilizing optical isolation provided by the optical cable, it is possible to permit other machines, even those generating electrical noise to be hooked up to the patient without compromising or creating ground current which could have deleterious effects on the patient or the signal outputs received from the head of the patient.

The construction of the headpiece, the associated apparatus and system makes it possible to utilize the same in connection with various types of EEGs, as for example, resting EEG monitoring during surgical procedures or in conjunction with sleep studies. These are all made readily possible because of the use of an isolating optical cable for connecting the headpiece to the equipment.

The elasticity of the headpiece 21 permitting stretching of the strips between electrode assemblies 31 makes it possible for the headpiece 21 to fit various head sizes and still provide accurate positioning of the electrodes, as for example, in the 10–20 system. It should be appreciated that the headpiece 21 of the present invention can be utilized with other electrode positioning systems. By providing amplifiers and circuitry adjacent to the body of the patient, as for example, on the neck of the patient as heretofore described, there is less need for preparation of the skin to obtain good contact because there is no need to provide signals over long conducting wires which have a tendency to pick up noise from the ambient from 60 cycle sources as well as other sources providing electrical disturbances.

The system of the present invention makes it possible to greatly improve the signal-to-noise ratio. The system eliminates the need for extensive skin preparation. It also gives the patient mobility and isolates the patient from other machines. The single use disposable dry electrodes which are utilized are easy to use and provide good electrical conductivity. When a procedure is completed, the electrodes 41 are easily removed permitting ready re-use of the headpiece 21.

By providing the two ear reference channels to the standard EEG equipment, in addition to the 19 channels of the 10–20 system, existing machines can be utilized because by providing all 21 channels, the machine is led to believe that it is connected directly to the patient rather than to the apparatus and system of the present invention. By providing two additional channels to provide the information typically obtained from reference electrodes near the ears, any electrode system may be used. The battery testing information is transferred to battery test circuitry which is often remote from the patient. A smaller size headpiece can be made for use with infants. Such a system can be used for evoked potential and/or conventional EEG measurements.

Figure 17:
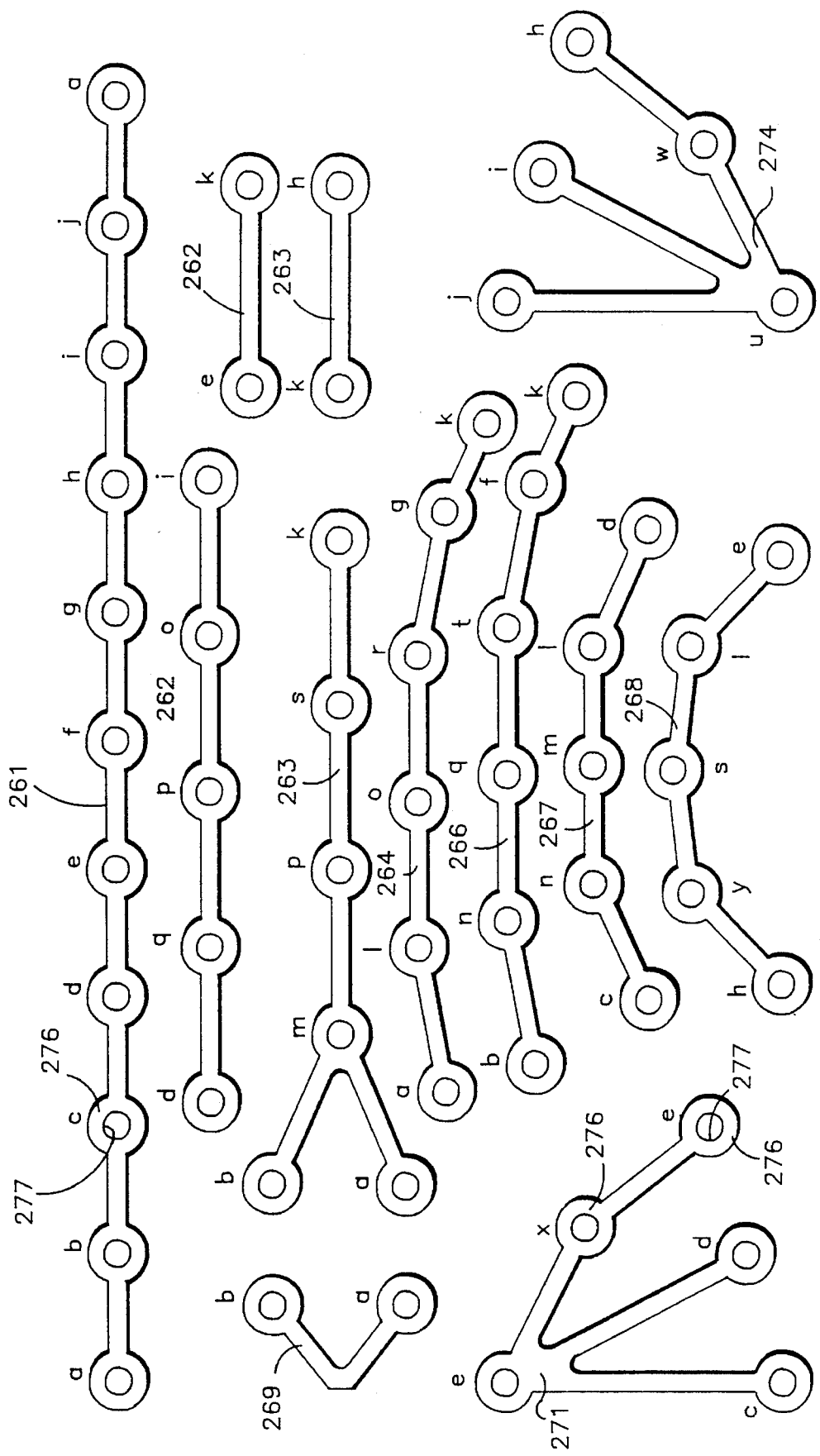
FIG. 17 is a plan view of alternative elastic strips for use in another embodiment of a headpiece of the present invention.

In connection with the present invention, it has been found that is may be desirable to construct the headpiece 21 as shown in FIG. 17 from elastic strips 261, 262, 263, 264, 266, 267, 268, 269, 271, 272, 273 and 274. These elastic strips can be formed of the same material as the strips 22 and 23 hereinbefore described. However, the strips shown in FIG. 17 have the advantage in that they can be die cut without the necessity of cutting in openings 26 as in the previous headpiece 21. The strips 261–274 hereinbefore described are provided with junctions 276 having holes 277 therein. As can be seen, the strips 261–274 are numbered with the appropriate letters so that they can be assembled to provide the headpiece 21 hereinbefore described. The strips 261–274 shown in FIG. 17 facilitate manufacturing and operations for a headpiece 21. By providing the strips 261–274 shown in FIG. 17 the length of the strips between the junctions 266 can be covered by sleeves (not shown) which can be continuous and need not be separated and wrapped and sealed as in the previous embodiment of the headpiece 21. In other words, such sleeves can be slipped over the wires or conductors (not shown) and over one end of each of the strips 261–274 and positioned over the portions of the strips 261–274 between the junctions 266.

Figure 12:
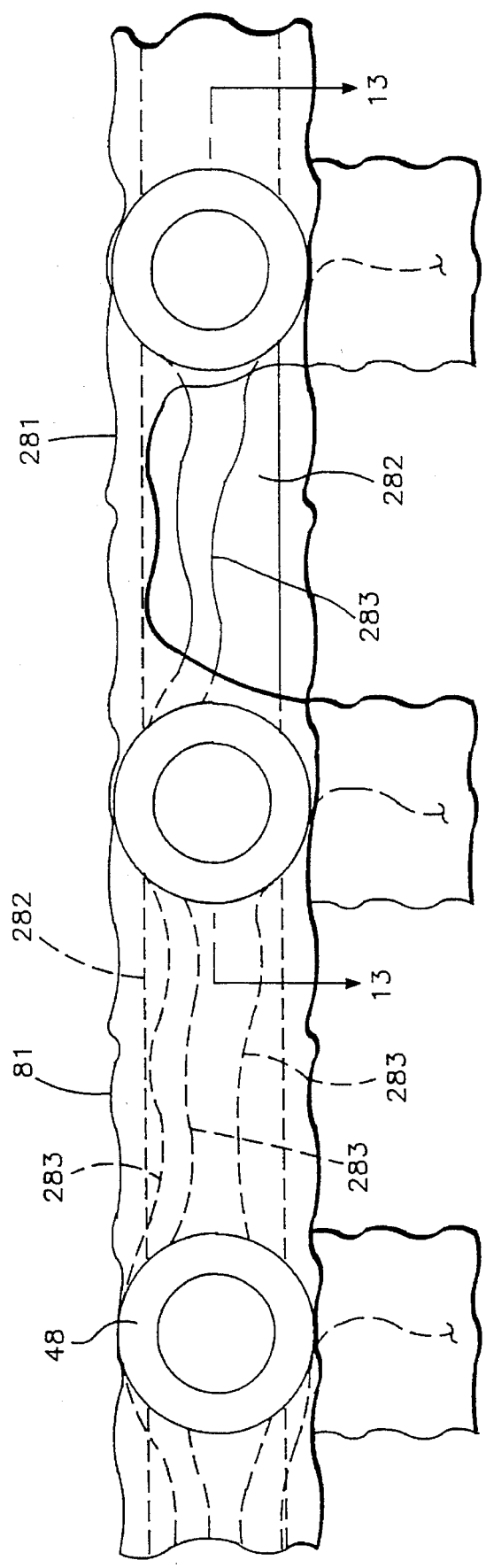
FIG. 12 is a view of a portion of a headpiece incorporating another embodiment of the invention.
Figure 13:
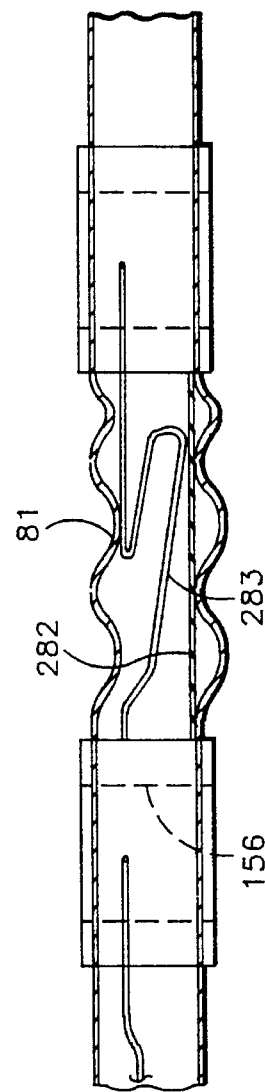
FIG. 13 is a cross-sectional view taken along the line 13—13 of FIG. 12.

In connection with the foregoing, it has been assumed that separate wires or conductors 68 have been utilized in the headpiece. However it should be appreciated that in place thereof flexible tape cables 281 can be provided as shown in FIGS. 12 and 13, in which the tape cables are comprised of flat plastic stock in the form of strips 282 having adherent thereto conductors 283 extending longitudinally thereof which have been formed in a suitable manner such as by etching to provide the connections between the electrode holders 48 to perform the same functions as the conductors 68 hereinbefore described. In order to accommodate the stretching of the elastic strips 22 and 23, the tape cables 281 are folded over themselves in a serpentine fashion such as shown in FIGS. 12 and 13 to permit the spacing between the electrode holders 48 to vary depending upon the size of the head of the patient on which the headpiece is placed. The conductors on the tape cables can be secured to make electrical connections to the tabs 72 engaging the electrodes 41, as for example by appropriate solder joints (not shown).

From the foregoing, it can be seen that there has been provided an EEG headpiece with disposable electrodes, an apparatus, system and method for use therewith which has many features and advantages.

What is claimed:

1. A headpiece for making EEG measurements on the head of a patient in the form of a human being utilizing an electrode positioning system requiring the use of a plurality of electrodes in predetermined anatomical positions on the head of the patient, the head having a front, a back and first and second sides, the front having a chin with a frontal portion comprising, a plurality of longitudinally extending and transversely extending elastic strips of an elastic material forming a pattern having openings therein, a plurality of electrode assemblies mounted on said strips of material in spaced-apart positions, means secured to said strips for securing said strips and the electrode assemblies mounted thereon to the head of the patient after stretching of the strips so that the electrode assemblies are positioned in the desired anatomical positions on the head of the patient regardless of the size of the head of the patient and hold-down means secured to the strips for securing the strips to the head of the patient after the strips have been stretched so that they extend over the front, rear and first and second sides of the head of the patient, said hold-down means including first and second straps depending from the first and second sides of the head of the patient and strap means secured to the first and second straps extending forwardly from the first and second straps and including a frontal portion adapted to extend over and engage the frontal portion of the chin of the patient, said frontal portion of the strap means lying in a plane which is substantially perpendicular to the neck of the patient when engaging the frontal portion of the chin of the patient.

2. A headpiece as in claim 1 wherein the strips extend in directions which are at an angle with respect to each other to provide a criss-cross pattern.

3. A headpiece as in claim 1 together with removable electrodes disposed in each of the electrode assemblies.

4. A headpiece for making EEG measurements on the head of a patient in the form of a human being utilizing an electrode positioning system requiring the use of a plurality of electrodes in predetermined anatomical positions on the head of the patient comprising, a plurality of longitudinally extending and transversely extending strips of an elastic material forming a pattern having openings therein, a plurality of electrode assemblies mounted on said strips of material in spaced-apart positions, means secured to said strips for securing said strips and the electrode assemblies mounted thereon to the head of the patient by stretching of the strips so that the electrode assemblies are positioned in the desired anatomical positions on the head of the patient regardless of the size of the head of the patient, said strips being provided with junctions, said junctions having centrally disposed holes therein, said electrode assemblies being mounted in said holes and having outer and inner sides, said electrode assemblies having openings therein extending through the inner and outer sides and toward the head of the patient, said openings being open and accessible on the outer side so that the electrodes can be inserted from the outer side and placed in contact with the head of the patient and retaining means carried by the electrode assemblies adapted to retain said electrodes within the electrode assemblies and adapted to make electrical contact therewith.

5. In a headpiece for making EEG measurements on the head of a patient in the form of a human being utilizing an electrode positioning system requiring the use of a plurality of electrodes in predetermined anatomical positions on the head of the patient, a plurality of longitudinally extending and transversely extending strips of an elastic material forming a pattern having openings therein, a plurality of electrode assemblies mounted on said strips of material in spaced-apart positions, means secured to said strips for securing said strips and the electrode assemblies mounted thereon to the head of the patient by stretching of the strips so that the electrode assemblies are positioned in the desired anatomical positions on the head of the patient regardless of the size of the head of the patient, said strips being provided with junctions, said junctions having centrally disposed holes therein, said electrode assemblies being mounted in said holes and having outer and inner sides, said electrode assemblies having openings therein extending through the inner and outer sides and toward the head of the patient, said openings being open and accessible on the outer side, electrodes disposed in the openings in the electrode assemblies and adapted to be in contact with the head of the patient and retaining means carried by the electrode assemblies for retaining said electrodes within the electrode assembly and making electrical contact therewith, said retaining means including yieldable spring members engaging the electrodes and only permitting movement of the electrodes in the holes of the electrode assemblies in a direction toward the head of the patient.

6. A headpiece for making EEG measurements on the head of a patient in the form of a human being utilizing an electrode positioning system requiring the use of a plurality of electrodes in predetermined anatomical positions on the head of the patient, the head having a front, a back and first and second sides, the front having a chin with a frontal portion comprising, a plurality of longitudinally extending and transversely extending elastic strips of an elastic material which cross each other at junctions to form a pattern having openings therebetween, a plurality of electrode assemblies mounted on said elastic strips of material in spaced-apart positions and means secured to said elastic strips for securing said elastic strips and the electrode assemblies mounted thereon to the head of the patient after stretching of the strips so that the electrode assemblies are positioned in the desired anatomical positions on the head of the patient, said means secured to said strips including depending straps depending alongside the first and second sides of the head of the patient and strap means secured to the depending strips and including a frontal portion adapted to be secured to the head of the patient and to extend over the frontal portion of the chin.

7. A headpiece as in claim 6 together with an electronics module and cabling connecting the electronics module to the electrodes of the electrode assemblies.

8. A headpiece as in claim 7 together with a battery pack connected to the electronics module to supply power to the electronics module.

9. A headpiece as in claim 8 together with a reference mounted in the neckband adapted to engage the neck of the patient.

10. A headpiece as in claim 7 wherein said cabling includes electrical conductors connected to the electrodes of the electrode assemblies and extending to the rear of the headpiece.

11. A headpiece for making EEG measurements on the head of a patient in the form of a human being and utilizing an electrode positioning system requiring the use of a plurality of electrodes in predetermined anatomical positions on the head of the patient, the head having an adjoining neck and a chin comprising a plurality of longitudinally extending and transversely extending elastic strips of an elastic material which cross each other at junctions to form a pattern having openings therebetween, a plurality of electrode assemblies mounted on said elastic strips of material in spaced-apart positions and means secured to said elastic strips adapted to secure said elastic strips and the electrode assemblies mounted thereon to the head of the patient by stretching of the strips so that the electrode assemblies are positioned in the desired anatomical positions on the head of the patient, said means secured to said elastic strips including straps secured to the elastic strips to hold the elastic strips in place on the head of the patient, said straps including a neck strap being sized and formed and adapted to engage at least a portion of the neck of the patient and a chin strap sized and formed and adapted to engage the chin of the patient.

12. A headpiece for making EEG measurements on the head of a patient in the form of a human being utilizing an electrode positioning system requiring the use of a plurality of electrodes in predetermined anatomical positions on the head of the patient comprising a plurality of longitudinally extending and transversely extending elastic strips of an elastic material which cross each other at junctions to form a pattern having openings therebetween, a plurality of electrode assemblies mounted on said elastic strips of material in spaced-apart positions, means secured to said elastic strips for securing said elastic strips and the electrode assemblies mounted thereon to the head of the patient by stretching of the strips so that the electrode assemblies are positioned in the desired anatomical positions on the head of the patient, said means secured to said strips including straps secured to the elastic strips to hold the headpiece in place on the head of the patient and sheaths extending around the elastic strips and the electrical conductors to prevent the elastic strips from coming into contact with the hair on the head of the patient.

13. A headpiece as in claim 12 wherein the elastic strips have free length portions and wherein said conductors have lengths which are greater than the free length portions of the strips to permit stretching of the elastic strips to accommodate different sizes of heads of patients.

14. In a headpiece for making EEG measurements on the head of a patient in the form of a human being utilizing an electrode positioning system requiring the use of a plurality of electrodes in predetermined anatomical positions on the head of the patient, a plurality of longitudinally extending and transversely extending elastic strips of an elastic material which cross each other at junctions to form a pattern having openings therebetween, a plurality of electrode assemblies mounted on said elastic strips of material in spaced-apart positions and means secured to said elastic strips for securing said elastic strips and the electrode assemblies mounted thereon to the head of the patient after stretching of the strips so that the electrode assemblies are positioned in the desired anatomical positions on the head of the patient, said means secured to said strips including straps secured to the headpiece adapted to be secured to the head of the patient to hold the headpiece in place on the head of the patient, the electrode assemblies being positioned at the junctions and being constructed to fasten the elastic strips together at the junctions, said electrode assemblies having holes therein extending therethrough and having first and second ends with the first ends adapted to face toward the head of the patient and the second ends adapted to face away from the head of the patient, the second ends of the holes being accessible in a direction towards the head of the patient to permit electrodes to be inserted into the holes through the second ends of the holes, said electrode assemblies including retaining means adapted to retain said electrodes in said electrode assemblies and to make electrical contact therewith.

15. In a headpiece for making EEG measurements on the head of a patient in the form of a human being utilizing an electrode positioning system requiring the use of a plurality of electrodes in predetermined anatomical positions on the head of the patient, a plurality of longitudinally extending and transversely extending elastic strips of an elastic material which cross each other at junctions to form a pattern having openings therebetween, a plurality of electrode assemblies mounted on said elastic strips of material in spaced-apart positions, means secured to said elastic strips for securing said elastic strips and the electrode assemblies mounted thereon to the head of the patient by stretching of the strips so that the electrode assemblies are positioned in the desired anatomical positions on the head of the patient, said means secured to said strips including straps secured to the headpiece adapted to be secured to the head of the patient to hold the headpiece in place on the head of the patient, said electrode assemblies fastening the elastic strips together at the junctions, an electrical conductor connected to each of said electrode assemblies, certain of said conductors extending alongside a plurality of electrode assemblies, each of said electrode assemblies including snap fastening means for securing said each electrical conductor and said certain conductors when present to that electrode assembly.

16. A headpiece for making EEG measurements on the head of a patient in the form of a human being utilizing an electrode positioning system requiring the use of a plurality of electrodes in predetermined anatomical positions on the head of the patient comprising a plurality of longitudinally extending and transversely extending strips of an elastic material forming a pattern having openings therein, a plurality of electrode assemblies mounted on said strips of material in spaced-apart positions, means secured to said strips for securing said strips and the electrode assemblies mounted thereon to the head of the patient by stretching of the strips so that the electrode assemblies are positioned in the desired anatomical positions on the head of the patient regardless of the size of the head of the patient, said headpiece carrying preauricular marks.

17. A system for making EEG measurements on the head of a patient in the form of a human being using an electrode positioning system requiring the use of a plurality of electrodes in predetermined anatomical positions on the head of the patient, the head of the patient having a front, back and first and second sides, the front having a chin with a frontal portion comprising a headpiece adapted to be secured to the head of the patient, said headpiece being comprised of a plurality of strips extending in one direction and a plurality of strips extending in a different direction to provide a criss-cross pattern having openings therein, said strips being formed of an elastic material, a plurality of electrode assemblies mounted on said strips in predetermined positions, means adapted to secure the headpiece to the head of the patient and including straps secured to said strips and adapted to depend along the first and second sides of the head of the patient and strap means secured to said straps and adapted to extend forwardly over the frontal portion of the chin of the patient, said strips being of a length so that the strips must be stretched at least a certain amount to fit on the head of the patient, said strips permitting stretching so that the electrodes are positioned in the desired anatomical positions on the head of the patient regardless of the size of the head of the patient electrical circuitry adapted to be carried by the patient and electrically connected to the electrode assemblies for providing electrical signals in a plurality of channels and means for analyzing said electrical signals.

18. A system as in claim 17 wherein the electrical circuitry adapted to be carried by the patient includes a multiplexer having an input for receiving the electrical signals from the electrode assemblies and an output, an analog-to-digital converter connected to the output of the multiplexer to form a serial-to-parallel converter connected to the analog-to-digital converter and supplying a serial output, a pulse-width modulator connected to the parallel-to-serial converter to provide a pulse-width modulated signal, a serial-to-parallel converter for receiving the pulse-width modulated signal to supply parallel data, a digital-to-analog converter for converting the parallel data into analog information, a demultiplexer for converting the analog information into a plurality of channels corresponding to the signals in the channels received from the electrode assemblies on the headpiece on the head of the patient and conventional means for analyzing the signals in the channels.

19. A system as in claim 18 together with means for detecting the absence of an electrode in the headpiece or detecting a high impedance contact between the electrode and the skin on the head of the patient.

20. A system for making EEG measurements on the head of patient in the form of a human being using an electrode positioning system requiring the use of a plurality of electrodes in predetermined anatomical positions on the head of the patient comprising, a headpiece adapted to be secured to the head of the patient, said headpiece being comprised of a plurality of strips extending in one direction and a plurality of strips extending in a different direction to provide a criss-cross pattern having openings therein, said strips being formed of an elastic material, a plurality of electrode assemblies mounted on said strips in predetermined positions, means for securing the headpiece to the head of the patient and including means extending over the chin of the patient, said strips being of a length so that the strips must be stretched at least a certain amount to fit on the head of the patient, said strips permitting stretching so that the electrodes are positioned in the desired anatomical positions on the head of the patient regardless of the size of the head of the patient, electrical circuitry adapted to be carried by the patient and electrically connected to the electrode assemblies for providing electrical signals in a plurality of channels and means for analyzing said electrical signals, said electrical circuitry adapted to be carried by the patient including a multiplexer having an input for receiving the electrical signals from the electrode assemblies and an output, an analog-to-digital converter connected to the output of the multiplexer, to form a parallel-to-serial converter connected to the analog-to-digital converter and supplying a serial output, a pulse-width modulator connected to the parallel-to-serial converter to provide a pulse-width modulated signal, a serial-to-parallel converter for receiving the pulse-width modulated signal to supply parallel data, a digital-to-analog converter for converting the parallel data into analog information, a demultiplexer for converting the analog information into a plurality of channels corresponding to the signals in the channels received from the electrode assemblies on the headpiece on the head of the patient, conventional means for analyzing the signals in the channels and means for detecting the absence of an electrode in the headpiece or detecting a high impedance contact between the electrode and the skin on the head of the patient, said means for detecting including visual indicating means for visually indicating the specific electrode which is indicated to be absent or which is making a high impedance contact.

21. A system for making EEG measurements on the head of patient in the form of a human being using an electrode positioning system requiring the use of a plurality of electrodes in predetermined anatomical positions on the head of the patient comprising, a headpiece adapted to be secured to the head of the patient, said headpiece being comprised of a plurality of strips extending in one direction and a plurality of strips extending in a different direction to provide a criss-cross pattern having openings therein, said strips being formed of an elastic material, a plurality of electrode assemblies mounted on said strips in predetermined positions, means for securing the headpiece to the head of the patient and including means extending over the chin of the patient, said strips being of a length so that the strips must be stretched at least a certain amount to fit on the head of the patient, said strips permitting stretching so that the electrodes are positioned in the desired anatomical positions on the head of the patient regardless of the size of the head of the patient, electrical circuitry adapted to be carried by the patient and electrically connected to the electrode assemblies for providing electrical signals in a plurality of channels and means for analyzing said electrical signals, the electrical circuitry being adapted to be carried by the patient including a multiplexer having an input for receiving the electrical signals from the electrode assemblies and an output, an analog-to-digital converter connected to the output of the multiplexer, a parallel-to-serial converter connected to the analog-to-digital converter and supplying a serial output, a pulse-width modulator connected to the parallel-to-serial converter to provide a pulse-width modulated signal, a serial-to-parallel converter for receiving the pulse-width modulated signal to supply parallel data, a digital-to-analog converter for converting the parallel data into analog information, a demultiplexer for converting the analog information into a plurality of channels corresponding to the signals in the channels received from the electrode assemblies on the headpiece on the head of the patient, conventional means for analyzing the signals in the channels, an interface box, said interface box having a front panel, said front panel having thereon a representation of a head representing the head of the patient, said representation of a head on said front panel having sockets therein corresponding to all of the electrode positions on the head of the patient, said conventional means including a conventional EEG measuring apparatus having a control console with a representation of a head of a patient thereon with sockets positioned in accordance with all of the electrodes on the head of the patient and means connecting the channels of electrical signals supplied by the demultiplexer to all of the sockets of the interface box and to all of the sockets of the control console.

22. A method for making EEG measurements from a patient in the form of a human being having a head including using a headpiece having a plurality of electrodes positioned in predetermined anatomical positions on the head of the patient comprising, receiving electrical signals from the electrodes on the patient in a plurality of channels in parallel form, multiplexing the electrical signals and delivering the multiplexed signals form the patient to a position remote from the patient, demultiplexing the electrical signals, performing operations on all of the electrical signals to provide EEG signals which correspond to the EEG signals received from the leads coupled directly to the head of the patient and analyzing the EEG signals using conventional EEG apparatus.

23. A method as in claim 22 wherein the electrical signals from the electrodes are in analog form, together with the steps of converting the multiplexed information in parallel form from analog-to-digital form, converting the information in parallel form to serial form, converting the serial form information from digital-to-analog form, converting the analog information from serial-to-parallel form into a plurality of channels corresponding to the electrical information received from the electrodes on the head of the patient.

24. A system for making EEG measurements on the head of patient in the form of a human being using an electrode positioning system requiring the use of a plurality of electrodes in predetermined anatomical positions on the head of the patient comprising a headpiece adapted to be secured to the head of the patient, said headpiece being comprised of a plurality of elastic strips extending in one direction and a plurality of elastic strips extending in a different direction to provide a criss-cross pattern having openings therein, a plurality of electrode assemblies mounted on said strips in predetermined positions, so that portions of said elastic strip are disposed between electrode assemblies, said elastic strips being of a length so that the elastic strips must be stretched at least a certain amount to fit on the head of the patient, said elastic strips being capable of being stretched so that the electrodes are positioned in the desired anatomical positions on the head of the patient regardless of the size of the head of the patient, electrical circuitry adapted to be carried by the patient and electrically connected to the electrode assemblies for providing electrical signals in a plurality of channels, said electrical circuitry including a conductor connected to each of said electrode assemblies, said conductor for each electrode assembly being disposed along the length of an elastic strip and extending between electrode assemblies and having a length which is greater than the length of the corresponding portion of each elastic strip when it is not stretched to permit the headpiece to be stretched over the head of the patient.

25. In a system for making EEG measurements on the head having hair thereon of a patient in the form of a human being using an electrode positioning system requiring the use of a plurality of electrodes in predetermined anatomical positions on the head of the patient, a headpiece adapted to be secured to the head of the patient, said headpiece being comprised of a plurality of elastic strips extending in one direction and a plurality of elastic strips extending in a different direction to provide a criss-cross pattern having openings therein, a plurality of electrode assemblies mounted on said strips in predetermined positions, so that portions of said elastic strip are disposed between electrode assemblies, said elastic strips being of a length so that the elastic strips must be stretched at least a certain amount to fit on the head of the patient, said elastic strips being capable of being stretched so that the electrodes are positioned in the desired anatomical positions on the head of the patient regardless of the size of the head of the patient, electrical circuitry adapted to be carried by the patient and electrically connected to the electrode assemblies for providing electrical signals in a plurality of channels, said electrical circuitry including a conductor connected to each of said electrode assemblies, said each conductor being disposed along the length of a strip and extending between electrode assemblies and having a length which is greater than the length of the corresponding portion of the elastic strip when it is not stretched to permit the headpiece to be stretched over the head of the patient and sheaths extending around said portions of said elastic strips and over the conductors serving to prevent the elastic strips from coming into contact with the hair on the head of the patient.

26. A system for making EEG measurements on the head of a patient in the form of a human being having a head with hair thereon, utilizing an electrode positioning system requiring the use of a plurality of electrodes in predetermined anatomical positions on the head of the patient comprising a headpiece adapted to be secured to the head of the patient, said headpiece being comprised of a plurality of elastic strips extending in one direction and a plurality of elastic strips extending in a different direction to provide a criss-cross pattern having openings therein, a plurality of electrode assemblies mounted on said elastic strips in predetermined positions, means for securing the headpiece to the head of the patient, said elastic strips being of a length so that the strips must be stretched at least a certain amount to fit on the head of the patient, said elastic strips permitting stretching so that the electrode assemblies are positioned in the desired anatomical positions on the head of the patient regardless of the size of the head of the patient, sheaths formed of a non-elastic material extending around the elastic strips between the electrode assemblies and serving to permit stretching of the elastic strips to prevent the elastic strips from grabbing the hair on the head of the patient and electrical circuitry adapted to be carried by the patient and electrically connected to the electrode assemblies for providing electrical signals from the electrode assemblies.

27. A system as in claim 26 wherein said electrical circuitry includes conductors connected to said electrode assemblies and wherein said conductors are disposed in said sheaths.

* * * * *